United States Patent [19]
Peterson et al.

[11] Patent Number: 6,121,042
[45] Date of Patent: *Sep. 19, 2000

[54] APPARATUS AND METHOD FOR SIMULATING IN VIVO CONDITIONS WHILE SEEDING AND CULTURING THREE-DIMENSIONAL TISSUE CONSTRUCTS

[75] Inventors: Alvin Peterson, Jamul; Lee K. Landeen; John Bennett, both of San Diego; Jason Gee, San Francisco, all of Calif.; Scott Chesla, Atlanta, Ga.; Joan Zeltinger, San Diego, Calif.; James H. Flatt, Del Mar, Calif.; Mark A. Applegate, San Diego, Calif.; Noushin Dunkelman, San Diego, Calif.; Stephen V. Kemmerrer, San Diego, Calif.

[73] Assignee: Advanced Tissue Sciences, Inc., La Jolla, Calif.

[*] Notice: This patent is subject to a terminal disclaimer.

[21] Appl. No.: 09/001,609

[22] Filed: Dec. 31, 1997

Related U.S. Application Data

[63] Continuation-in-part of application No. 08/478,309, Jun. 7, 1995, Pat. No. 5,846,828, and a continuation-in-part of application No. 08/912,948, Aug. 14, 1997, Pat. No. 6,060,306, which is a continuation of application No. 08/486,185, Jun. 7, 1995, abandoned, application No. 08/672,697, Jun. 27, 1996, Pat. No. 5,792,603, which is a continuation-in-part of application No. 08/430,768, Apr. 27, 1995, abandoned.

[51] Int. Cl.⁷ .............................. C12M 3/00; C12N 5/00
[52] U.S. Cl. ................................. 435/284.1; 435/286.5; 435/297.2; 435/401
[58] Field of Search ............................ 435/1.2, 399, 401, 435/284.1, 1.1, 286.5, 286.6, 289.1, 293.1, 293.2, 297.2, 297.4, 301.1, 395, 398, 402; 600/36; 623/1, 2, 11, 13, 16; 73/789

[56] References Cited

U.S. PATENT DOCUMENTS

| | | |
|---|---|---|
| 3,734,851 | 5/1973 | Matsumura . |
| 3,883,393 | 5/1975 | Knazek et al. . |
| 3,966,401 | 6/1976 | Hancock et al. . |

(List continued on next page.)

FOREIGN PATENT DOCUMENTS

| | | |
|---|---|---|
| WO 90/13639 | 11/1990 | WIPO . |
| WO 92/11355 | 7/1992 | WIPO . |
| WO 93/01843 | 2/1993 | WIPO . |
| WO 93/12805 | 7/1993 | WIPO . |
| WO 93/18132 | 9/1993 | WIPO . |
| WO 94/25584 | 11/1994 | WIPO . |

OTHER PUBLICATIONS

Atikinson et al.; *Biochemical Engineering and Biotechnology Handbook*; pp. 476–487 (1991).

Halberstadt et al., "The In Vitro Growth of a Three–Dimensional Human Dermal Replacement Using a Single–Pass Perfusion System," *Biotechnology and Bioengineering* 43:740–746 (1994).

(List continued on next page.)

*Primary Examiner*—William H. Beisner
*Attorney, Agent, or Firm*—Pennie & Edmonds LLP

[57] ABSTRACT

An apparatus and method for sterilizing, seeding, culturing, storing, shipping, and testing three-dimensional tissue constructs is disclosed. The apparatus includes a fluid reservoir, a pump, at least one treatment chamber, and a means for controlling media flow characteristics around a tissue construct disposed within the treatment chamber, and for controlling movement of the construct itself, so as to simulate a variety of physiologic conditions. One exemplary embodiment of the invention includes a means for applying an axial stress to the construct. Applying an axial stress to the construct during seeding and culturing results in a tissue-engineered construct with cells and their fibers oriented in a manner which is more likely to possess long term dimensional stability and the patency of native vessels with normal physiologic function.

38 Claims, 13 Drawing Sheets

U.S. PATENT DOCUMENTS

| | | |
|---|---|---|
| 4,015,590 | 4/1977 | Normann . |
| 4,050,893 | 9/1977 | Hancock et al. . |
| 4,372,743 | 2/1983 | Lane . |
| 4,417,861 | 11/1983 | Tolbert . |
| 4,546,642 | 10/1985 | Swanson . |
| 4,639,422 | 1/1987 | Geimer et al. . |
| 4,804,628 | 2/1989 | Cracauer et al. . |
| 4,835,102 | 5/1989 | Bell et al. ................................. 435/29 |
| 4,839,280 | 6/1989 | Banes . |
| 4,908,013 | 3/1990 | Muller et al. . |
| 4,911,713 | 3/1990 | Sauvage et al. . |
| 4,988,623 | 1/1991 | Schwarz et al. . |
| 5,026,650 | 6/1991 | Schwarz et al. . |
| 5,035,708 | 7/1991 | Alchas et al. . |
| 5,043,260 | 8/1991 | Jauregul . |
| 5,081,035 | 1/1992 | Halberstadt et al. . |
| 5,153,131 | 10/1992 | Wolf et al. . |
| 5,153,132 | 10/1992 | Goodwin et al. . |
| 5,153,133 | 10/1992 | Schwarz et al. . |
| 5,153,136 | 10/1992 | Vandenburgh . |
| 5,155,034 | 10/1992 | Wolf et al. . |
| 5,155,035 | 10/1992 | Schwarz et al. . |
| 5,176,153 | 1/1993 | Eberhardt . |
| 5,217,899 | 6/1993 | Shapiro et al. . |
| 5,230,693 | 7/1993 | Williams et al. . |
| 5,266,480 | 11/1993 | Naughton et al. . |
| 5,272,909 | 12/1993 | Nguyen et al. . |
| 5,279,612 | 1/1994 | Eberhardt . |
| 5,308,764 | 5/1994 | Goodwin et al. . |
| 5,376,110 | 12/1994 | Tu et al. . |
| 5,406,853 | 4/1995 | Lintilhac et al. . |
| 5,662,705 | 9/1997 | Love et al. . |
| 5,686,303 | 11/1997 | Korman . |
| 5,700,688 | 12/1997 | Lee et al. .............................. 435/287.1 |
| 5,792,603 | 8/1998 | Dunkelman et al. . |

OTHER PUBLICATIONS

Kanda et al., "Behavior of arterial wall cells cultured on periodically stretched substrates," *Cell Transplantation* 2:pp. 475–484, 1993.

BIOSIS abstract, AN 89:445182. Dartsch et al. 'Response of cultured endothelial cells to mechanical stimulation.' Basic Res. Cardio. vol. 84 (1989), pp. 268–281.

Bengtsson et al. "Endothelialization of Mechanical Heart Valves." J. Heart Valve Dis. vol. 2 (May, 1993), pp. 352–355.

Eskin et al. "Behavior of Endothelial Cell Cultured on Silatic . . . " Art. Organs. vol. 7 (1983), pp. 31–37.

Schima et al. "Mechanical Simulation of Shear Stress . . . " J. Biomech. vol. 23 (1990), pp. 845–851.

Van Wachem, et al. "Vacuum cell seeding:." Biomaterials. vol. 11 (Oct. 1990), pp. 602–606.

APPARATUS AND METHOD FOR SIMULATING IN VIVO CONDITIONS WHILE SEEDING AND CULTURING THREE-DIMENSIONAL TISSUE CONSTRUCTS

RELATED APPLICATIONS

This application is a continuation-in-part of U.S. patent application Ser. No. 08/478,309, filed Jun. 7, 1995, now U.S. Pat. No. 5,846,828, and entitled "Apparatus and Method for Sterilizing, Seeding, Culturing, Storing, Shipping, and Testing Tissue, Synthetic, or Mechanical Heart Valves or Valve Segments;" U.S. patent application Ser. No. 08/912,948, now U.S. Pat. No. 6,060,306, filed Aug. 14, 1997 and entitled "Apparatus and Method for Sterilizing, Seeding, Culturing, Storing, Shipping, and Testing Replacement Cartilage Tissue Constructs," which is a continuation of U.S. patent application Ser. No. 08/486,185, now abandoned, filed Jun. 7, 1995 and entitled "Apparatus and Method for Sterilizing, Seeding, Culturing, Storing, Shipping, and Testing Replacement Cartilage Tissue Constructs;" and U.S. patent application Ser. No. 08/672,697, filed Jun. 27, 1996, now U.S. Pat. No. 5,792,603, and entitled "Apparatus and Method for Sterilizing, Seeding, Culturing, Storing, Shipping, and Testing Tissue, Synthetic, or Native Vascular Grafts," which is a continuation-in-part of U.S. patent application Ser. No. 08/430,768, now abandoned, filed Apr. 27, 1995 and entitled "Apparatus and Method for Sterilizing, Seeding, Culturing, Storing, Shipping, and Testing Tissue, Synthetic, or Native Vascular Grafts."

Each of the above-referenced applications is hereby incorporated by reference.

BACKGROUND OF THE INVENTION

1. Technical Field

The present invention relates to the sterilization, seeding, culturing, storing, shipping, and testing of three-dimensional tissue. Specifically, the present invention relates to an apparatus and method for seeding and culturing three-dimensional tissue constructs with viable mammalian cells under simulated in vivo conditions, resulting in three-dimensional tissue that is more likely to display the biochemical, physical, and structural properties of native tissues.

2. Discussion of the Related Art

Biological implants are presently used by surgeons to repair or replace a variety of native tissues, including heart valves, arterial or venous blood vessels, articular cartilage, tendons, and ligaments, that are weakened, damaged or obstructed due to trauma or disease. Historically, implants have been either homografts, prosthetic grafts made of synthetic materials such as polyester (e.g., Dacron), expanded polytetraflouroethylene (ePTFE), and other composite materials, or fresh or fixed biological tissue grafts.

However, synthetic grafts generally have inadequate patency rates for many uses, while the harvesting of homografts requires extensive surgery which is time-consuming, costly, and traumatic to the patient. Fixed tissue grafts do not allow for infiltration and colonization by the host cells, which is essential to remodeling and tissue maintenance. Consequently, fixed tissue grafts degrade with time and will eventually malfunction.

Due to the inadequacies of these currently available synthetic and biological grafts, as well as the cost and limited supply of homografts, tissue-engineered grafts are being developed which are seeded and cultured, in vitro, with cells. For example, U.S. Pat. No. 5,266,480 to Naughton et al. discloses the establishment of a three-dimensional matrix, seeding of the matrix with desired cells, and maintenance of the culture to provide a variety of three-dimensional tissues suitable for use in different applications. Tissue-engineered grafts utilizing this technology may be superior to other grafts for use in replacement therapy in that they more closely display the long term dimensional stability and patency of native arteries and vessels with normal physiologic functionality.

Historically, the seeding and culturing of such grafts, and tissue in general, has taken place in a static environment such as a Petri or culture dish. However, there are disadvantages to seeding and culturing tissue in such an environment. For example, the lack of circulation of nutrients in these static systems results in a slow and ineffective seeding and culturing process. Moreover, a static culturing environment may lead to de-differentiation and loss of tissue function, and cannot support growth of tissue beyond a certain thickness.

In contrast, tissues that are seeded and cultured in a dynamic environment can be grown to a wider range of thicknesses, and are more likely to tolerate the physiological conditions that exist in the human body once implanted. Thus, there exists a need for an environment that is designed to simulate physiologic conditions that particular tissues would be subjected to in vivo, in which to seed and culture tissue-engineered grafts and other prosthetic devices.

SUMMARY OF THE INVENTION

It is therefore an object of the invention to provide an apparatus for seeding and culturing tissue constructs which is designed to simulate physiologic conditions that a particular construct would be subjected to in vivo by controlling the growth media flow through and across the construct, and the movement of the construct itself, to create varying physiologic-like pressures and forces which act upon the growing tissue.

It is a further object of the invention to stimulate the production of replacement tendon and ligament tissue constructs which display the critical biochemical, physical, and structural properties of native human tendon and ligament tissue by seeding and culturing the tissue in a dynamic environment.

It is a further object of the invention to provide a precise mechanical device with a minimum of moving parts to provide such environments.

It is yet a further object of the invention to provide a closed system free from contamination for sterilizing, seeding, culturing, storing, shipping, and testing tissue constructs.

In accordance with the present invention, there is provided an apparatus and method for seeding and culturing tissue constructs with viable mammalian cells under simulated in vivo conditions, resulting in three-dimensional tissue that is more likely to display the biochemical, physical, and structural properties of native tissues.

One exemplary embodiment of an apparatus according to the invention comprises a fluid reservoir, at least one construct treatment chamber, a support structure for supporting the construct in the treatment chamber, and a means for placing an axial load on the construct. By placing an axial load on the construct in the treatment chamber during culturing, an axial stress is placed on the construct. This stress results in a tissue-engineered tendon or ligament construct with cells and their fibers oriented in a manner which is more likely to possess long term dimensional stability and the patency of, for example, native tendons or ligaments with normal physiologic function. In this manner, one embodiment of the invention advantageously utilizes a mechanically non-complex apparatus to create a dynamic environment in which to seed and culture tissue-engineered tendons, ligaments or other implantable devices.

BRIEF DESCRIPTION OF THE DRAWINGS

These and other features, aspects, and advantages of the present invention will become more readily apparent from the following detailed description, which should be read in conjunction with the accompanying drawings in which:

FIGS. 5A–5C illustrate an apparatus according to the present invention for sterilizing, seeding, culturing, storing, shipping, and testing a cartilage prosthesis in which a piston and cylinder arrangement is utilized, wherein FIGS. 5B and 5C illustrate fluid flow during use;

FIGS. 7A–7B illustrate an alternative exemplary embodiment of the present invention for sterilizing, seeding, culturing, storing, shipping, and testing a prosthesis in which a bellows is utilized, wherein FIG. 7B is a cross-sectional view;

DETAILED DESCRIPTION OF THE INVENTION

Figure 1:
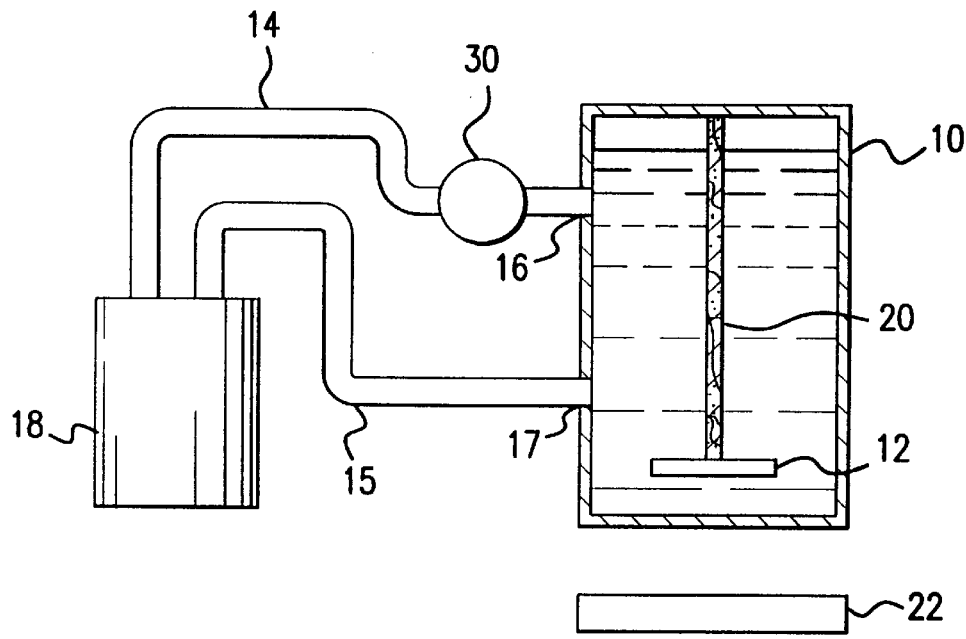
FIG. 1 illustrates an apparatus according to the present invention for sterilizing, seeding, culturing, storing, shipping, and testing a prosthesis in which a magnetic axial loading is utilized.

The following embodiments of the present invention will be described in the context of an apparatus and method for sterilizing, seeding, culturing, storing, shipping, and testing tendon and ligament constructs, although those skilled in the art will recognize that the disclosed methods and structures are readily adaptable for broader application. Note that whenever the same reference numeral is repeated with respect to different figures, it refers to the corresponding structure in each such figure.

FIG. 1 discloses a system for sterilizing, seeding, culturing, storing, shipping, and testing tendon and ligament constructs. According to a preferred embodiment of the invention, this system primarily comprises a treatment chamber 10, a pump 30, and a media reservoir 18 fluidly communicating with the treatment chamber.

Media reservoir 18 is used to store fluid for the system. Illustrative suitable reservoirs are the Gibco-BRL 1L media bag or any rigid container capable of sterilization. Reservoir 18 may include a one way sterile filter so as to provide a direct source of filtered gas to the fluid within the system or, alternatively, may include gas-permeable tubing or membranes comprised of a material such as silicone or Teflon so as to provide an indirect source of sterile gas to the system via diffusion. Examples of fluid which may be used in the system include, but are not limited to, sterilizing fluid, tanning fluid, cryopreservative fluid, rinse fluid, fluid containing cells, or fluid containing a culture medium. It is to be understood that during testing, seeding, and culturing in a preferred embodiment, the fluid is advantageously kept at human body temperature through use of an incubator, for example, and may be composed of a fluid which approximates the viscosity of human blood or other human bodily fluids.

The fluid contained in reservoir 18 is retrieved through either fluid line 14 or 15 into treatment chamber 10 through the action of pump 30, which, as discussed below, controls the flow of fluid within the system. Fluid lines 14 and 15, as well as all other fluid lines in the system, may be made of any type of stainless steel tubing or medical grade, sterilizable, durable, plastic tubing preferably comprised of a gas-permeable material such as silicone which is suitable for transporting the fluid in use.

Treatment chamber 10 is preferably composed of any biocompatible, rigid material capable of being sterilized such as Teflon, polycarbonate, PVC, stainless steel, acrylic, polypropelene, and polyethylene. Treatment chamber 10 may be a single piece of material or may comprise two or more sections which are secured and made leak proof through any standard means such as inner and outer threads, an o-ring seated in an annular groove, a clamp, or bonding agents. In order to view construct 20 within treatment chamber 10, a viewing port may be placed at any point on the chamber, or alternatively, the chamber may be made of an optically clear material such as polycarbonate or PVC. Ports 16 and 17 of treatment chamber 10 allow for the perfusion and/or circulation of fluid into and through chamber 10. Ports 16 and 17 are also used to attach treatment chamber 10 to fluid lines 14 and 15 respectively.

As mentioned, pump 30 controls the flow of the fluid within treatment chamber 10. Pump 30 may be any pump capable of providing unidirectional or bidirectional pulsatile or continuous pressure fluid flow in the system. Examples of such pumps include but are not limited to low flow pumps, invasive pumps such as a lobe-type pump, or non-invasive pumps such as a peristaltic pump. Thus, illustratively, when pump 30 is operating so as to force fluid from reservoir 18 to fluid line 14, and subsequently from fluid line 14 into chamber 10, fluid is forced from port 16 through chamber 10 to port 17. However, if pump 30 is operated so as to provide fluid flow in the opposite direction, fluid is then forced in an opposite direction from port 17 through chamber 10 to port 16.

It is to be understood that the pressure from pump 30 may be varied during use so as to provide varying pressure within treatment chamber 10. Moreover, it is to be understood that pump 30 may be operated bidirectionally in any manner and at any interval. Thus, pump 30 may be operated so as to provide bidirectional fluid flow in an alternating fashion at some predetermined interval. Alternatively, pump 30 may provide fluid flow in one direction for a predetermined period of time followed by fluid flow in the opposite direction for a similar period of time, or may provide fluid flow solely in one direction. Moreover, it is to be understood that, alternatively, one skilled in the art could devise a suitable valving system (e.g., through the use of a rotating valve) that could also provide chamber 10 with a bidirectional fluid flow.

Treatment chamber 10 is configured and dimensioned to house a tendon or ligament construct 20. Construct 20 may illustratively consist of any knitted, braided, woven, felted, or synthesized material that is bioresorbable and/or biocompatible, as well as any native material which will support appropriate cells. Treatment chamber 10 may be made any size so as to hold a construct 20 of any length or diameter. This is advantageous, as the system may be used to sterilize, seed, culture, store, ship, and test constructs of any size.

In a preferred embodiment of the present invention, construct 20 is secured to the top of treatment chamber 10 by any well known means. Such means include, but certainly are not limited to, sewing, lashing, adhesive bonding, clamping, welding, staking, pinching, or heat bonding.

A magnet 12 is attached to the lower end of construct 20 by any similarly well known means, such as those listed above. Magnet 12 may be comprised of any material that has the property of producing a magnetic field external to itself, including iron, steel or an alloy that has had this property artificially imparted. Alternatively, magnet 12 may be any material that has the property of being attracted by an external magnetic field.

As shown in FIG. 1, also included within the system is a magnetic field generator 22 for applying a magnetic field to magnet 12. Magnetic field generator 22 includes a device or material that is capable of producing a magnetic field, such as a magnetized bar of iron or steel, or a solenoid. Magnetic field generator 22 further includes a means for varying the magnetic field to be applied to magnet 12. If generator 22 includes a solenoid, the current applied to the solenoid may be varied so as to vary the strength of the solenoid's magnetic field. If generator 22 includes a bar magnet, it will also include a means for moving that magnet closer or nearer to magnet 12 so as to vary the magnetic field applied to magnet 12. One skilled in the art will appreciate that any well known method of imparting movement may be used to move the magnet, including a cam or motor driven push rod or screw. To place an axial load on construct 20, one skilled in the art will also appreciate that if magnet 12 is magnetized, field generator 22 need not also be magnetized, and need only comprise a material that is attracted by an external magnetic field.

By varying the magnetic field applied to magnet 12, the axial load on the construct may likewise be varied. It will thus be appreciated that the axial load may be varied to any extent and at any interval, or may be maintained as a constant. This is advantageous as the ideal axial load to be applied to the construct will vary with time due to the increasing density of the construct during seeding and culturing. Moreover, the ideal axial load to be applied necessarily depends from the outset on the original length and thickness of the construct, and may thus vary from treatment to treatment.

Perhaps most importantly, axial load variation is advantageous because stress is placed on construct 10 which resembles the physiological conditions typically encountered by tendons or ligaments in the human body. These culturing conditions are advantageous as they may improve the flow of nutrients to and removal of waste products from cells embedded in the construct. These conditions are also advantageous as they can be detected by living cells attached to construct 20, thus causing the cells to align and configure themselves in a manner more likely to tolerate the physiological conditions found in the human body.

Figure 2:
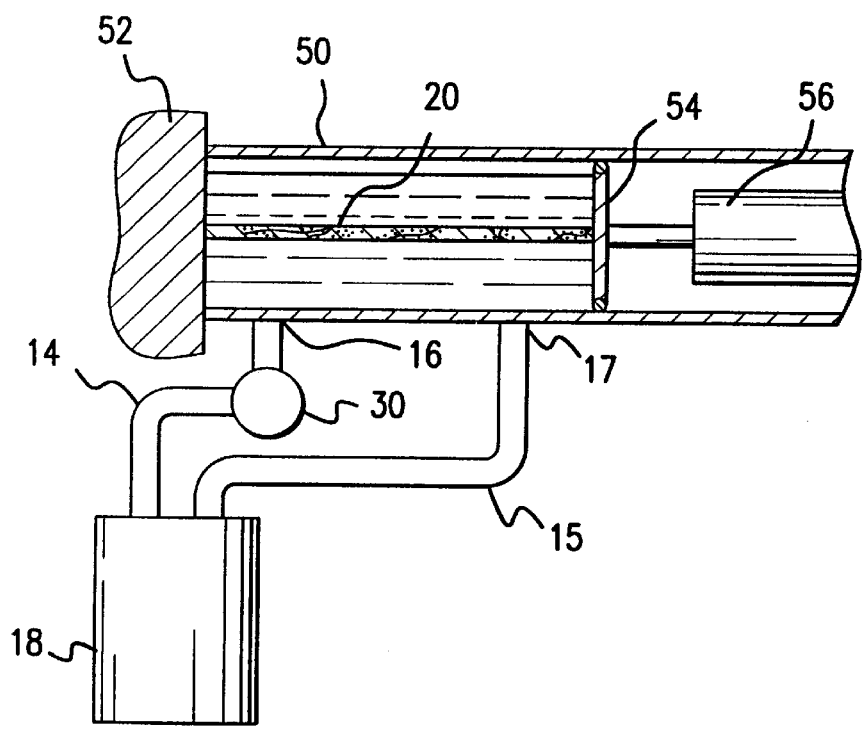
FIG. 2 illustrates an apparatus according to the present invention for sterilizing, seeding, culturing, storing, shipping, and testing a prosthesis in which a mechanical axial loading is utilized, and wherein the mechanical is generated using a piston.

FIG. 2 discloses an alternative embodiment of a system for sterilizing, seeding, culturing, storing, shipping, and testing tendon and ligament constructs. This system primarily comprises a treatment chamber 50, a pump 30, a piston 54, and a media reservoir 18 communicating with the treatment chamber.

Pump 30, media reservoir 18, fluid lines 14 and 15, ports 16 and 17, and the fluids which the system may contain are the same as those disclosed in conjunction with FIG. 1. Chamber 50 is identical to chamber 10, except chamber 50, unlike chamber 10, is sealed at one end by a piston. As with the system disclosed in FIG. 1, the fluid contained in reservoir 18 may be retrieved through fluid lines 14 or 15 into treatment chamber 50 through the action of pump 30, which controls the unidirectional or bidirectional flow and pressure of the fluid within the system. Also, as with the system disclosed in FIG. 1, construct 20 is secured to one end of treatment chamber 50. As set forth below, what differs from the embodiment disclosed in FIG. 1 is the means by which an axial load is placed on construct 20.

As shown in FIG. 2, the end of chamber 50 at which construct 20 is attached is also attached to a fixed structure 52. The opposite end of construct 20 is attached to a piston 54. Piston 54 is configured and dimensioned, using for example an o-ring, to create a hermetically sealed chamber 50. Force is applied to piston 54 in either direction by a force generator 56. Force generator 56 comprises any well known means for providing bidirectional linear force to a piston, such as an electrically-driven rotating cam, an electromechanical or pneumatic displacement device, or an electrically or pneumatically-driven lever arm. Alternatively, force may be applied to piston 54 by varying the fluid flow, and thus the pressure, within chamber 10. It is to be understood that the force applied to piston 54 may be varied so as to provide a varying axial load on construct 20 within treatment chamber 50 during use. As with the system disclosed in FIG. 1, this varying axial load is advantageous because stress is placed on construct 20 which resembles the physiological conditions typically encountered by tendons or ligaments in the human body. This is additionally advantageous as the ideal load to be applied to the construct will vary with time due to the increasing density of the construct during seeding and culturing. Moreover, the ideal load to be applied necessarily depends from the outset on the original length and thickness of the construct, and may thus vary from treatment to treatment.

Figure 3:
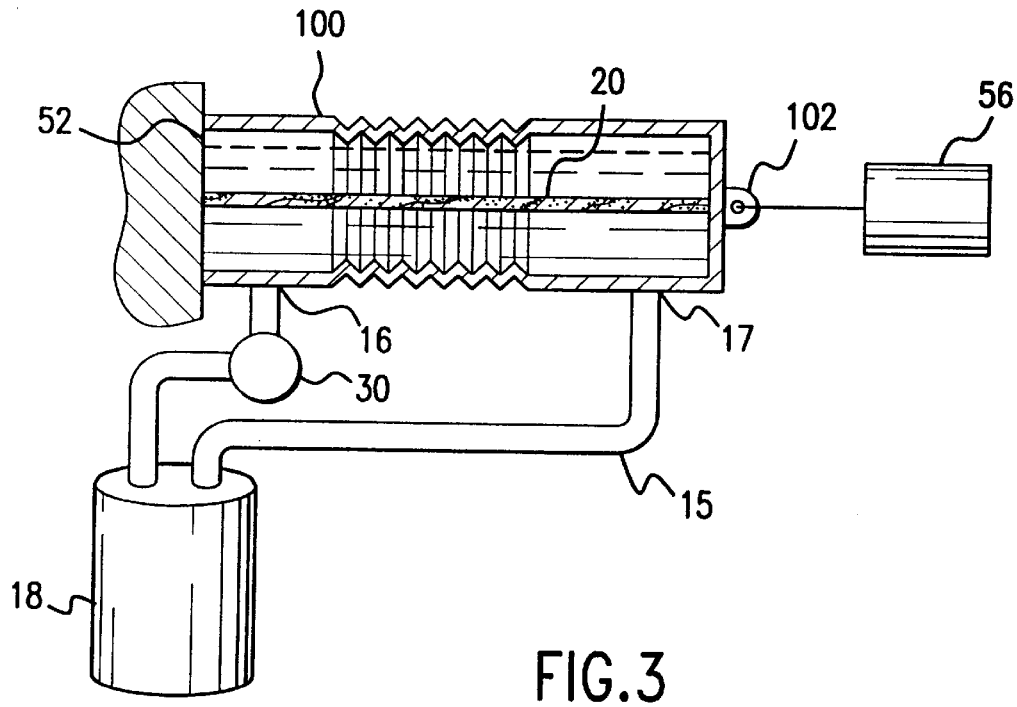
FIG. 3 illustrates an apparatus according to the present invention for sterilizing, seeding, culturing, storing, shipping, and testing a prosthesis in which a mechanical axial loading is utilized, and wherein the mechanical loading is generated using a bellows.

FIG. 3 discloses yet another alternative embodiment of the invention for sterilizing, seeding, culturing, storing, shipping, and testing tendon or ligament constructs. According to this alternative exemplary embodiment of the invention, the system primarily comprises a bellows 100, a pump 30, and a media reservoir 18.

Pump 30, media reservoir 18, fluid lines 14 and 15, ports 16 and 17, and the fluids which the system may contain are the same as those disclosed in conjunction with FIGS. 1 and 2. As with the systems disclosed in FIGS. 1 and 2, the fluid contained in reservoir 18 may be retrieved through fluid lines 14 or 15 into treatment chamber 10 through the action of pump 30, which controls the unidirectional or bidirectional flow and pressure of the fluid within the system.

Also, as with the system disclosed in FIG. 2, construct 20 is secured to one end of treatment chamber 10, with that end of chamber 10 likewise attached to a fixed structure 52. What differs from the embodiments disclosed in FIGS. 1 and 2 is the means by which an axial load is placed on construct 20. In particular, the opposite end of construct 20 is attached to bellows 100, rather than a piston or magnet.

Bellows 100 may comprise a hard-sided blow molded collapsible bellows cassette. However, one skilled in the art will understand that other types of bellows which include at least one rigid surface and flexible edges may be used. Bellows 100 may also include an external pull ring 102 for easy expansion, and may further include a sealable slit along one of the collapsible side walls so as to place construct 20 within the bellows for treatment. However, it is to be understood that a sealable slit may be placed at any location on bellows 100.

Construct 20 is attached to bellows 100 by any well known means, such as sutures, staples, or c-clips, or may be sandwiched between two opposable interlocking structures. Construct 20 may also be attached to bellows 100 by those attachment means mentioned in conjunction with FIG. 1.

As shown in FIG. 3, a force may be applied to bellows 100 by force generator 56 so as to apply an axial load to construct 20. As mentioned in conjunction with FIG. 2, force generator 56 comprises any well known means for providing force in two directions, such as an electrically-driven rotating cam, an electromechanical or pneumatic displacement device, or an electrically or pneumatically-driven lever arm. Alternatively, force may be applied to bellows 100 by varying the fluid flow, and thus pressure, within the bellows. It is also to be understood that the force applied to bellows 100 may be varied so as to provide a varying axial load on construct 20 within bellows 100 during use. Like the systems of FIGS. 1 and 2, an axial load is thus accomplished during seeding, culturing, and testing which closely resembles the physiological conditions found in the human body.

Figure 4:
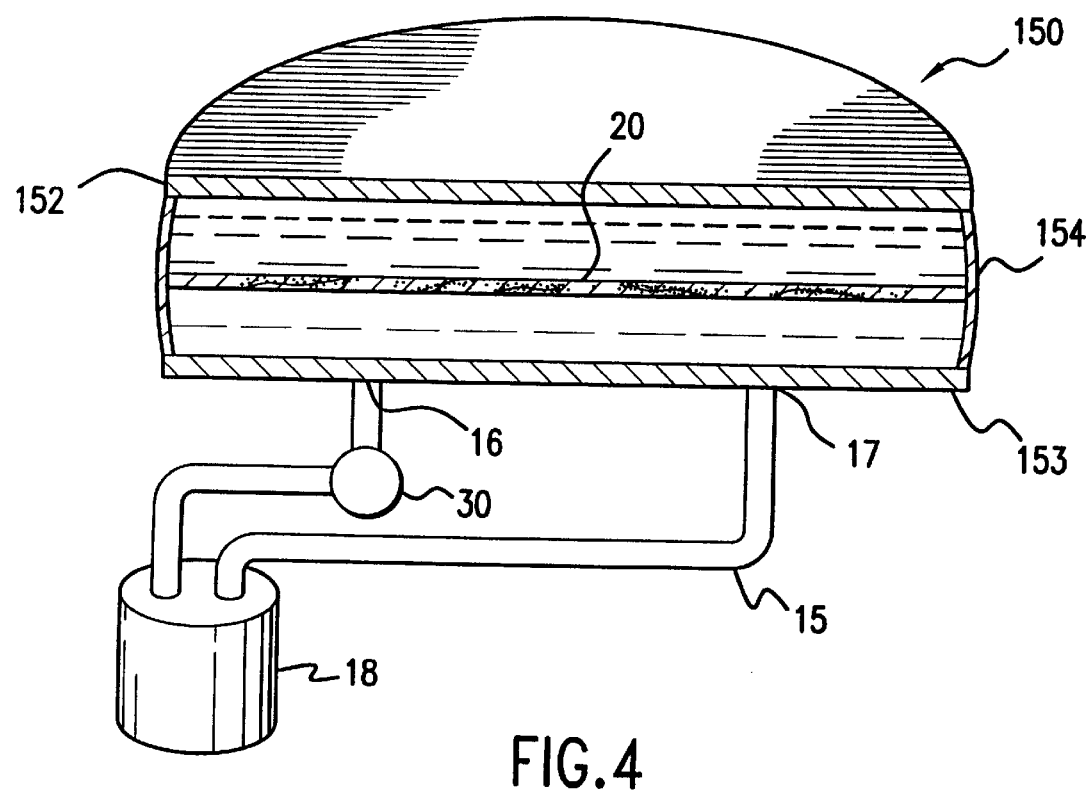
FIG. 4 illustrates yet another alternative exemplary embodiment of an apparatus according to the present invention for sterilizing, seeding, culturing, storing, shipping, and testing a prosthesis in which a flexible diaphragm is utilized to provide an axial load.

FIG. 4 discloses yet another alternative embodiment of the invention for sterilizing, seeding, culturing, storing, shipping, and testing tendon and ligament constructs. According to this alternative exemplary embodiment of the invention, the system primarily comprises a chamber 150, a pump 30, and a media reservoir 18. Pump 30, media reservoir 18, fluid lines 14 and 15, ports 16 and 17, and the fluids which the system may contain are the same as those disclosed in conjunction with FIGS. 1–3.

As shown in FIG. 4, chamber 150 comprises rigid upper and lower frame members 152 and 153 connected by a flexible diaphragm 154. Construct 20 is attached to opposing sides of flexible diaphragm 154 by any well known means, including those mentioned in conjunction with FIGS. 1 and 3.

In the exemplary embodiment of the invention disclosed in FIG. 4, pump 30 controls both the flow of the fluid within treatment chamber 150 and the pressure within that treatment chamber. Pump 30 may be any pump capable of providing unidirectional or bidirectional pulsatile or continuous pressure fluid flow in the system. Examples of such pumps include but are not limited to low flow pumps, invasive pumps such as a lobe-type pump, or non-invasive pumps such as a peristaltic pump. Thus, illustratively, when pump 30 is operating so as to force fluid from reservoir 18 to fluid line 14, and subsequently from fluid line 14 into chamber 150, fluid is forced from port 16 through chamber 150 to port 17. However, if pump 30 is operated so as to provide fluid flow in the opposite direction, fluid is then forced in an opposite direction from port 17 through chamber 150 to port 16.

It is to be understood that the pressure from pump 30 may be varied during use so as to provide varying pressure within treatment chamber 150. By varying the pressure from pump 30, flexible diaphragm 154 may be expanded and contracted. By expanding and contracting flexible diaphragm 154, a varying axial load is placed on construct 20, attached as mentioned to opposing sides of diaphragm 154. This varying axial load is advantageous because an axial stress is placed on construct 20 which resembles the physiological conditions typically encountered by tendons or ligaments in the human body. This is additionally advantageous as the ideal load to be applied to the construct will vary with time due to the increasing density of the construct during seeding and culturing. Moreover, the ideal load to be applied necessarily depends from the outset on the original length and thickness of the construct, and may thus vary from treatment to treatment.

In an alternative embodiment of the system disclosed in FIG. 4, only one port to chamber 150 is provided. As in the two-port embodiment, the one port may be used to circulate fluids into and out of treatment chamber 150, and to pressurize and depressurize chamber 150. One skilled in the art will understand that if only one port is used, pressure can be applied using, for example, a pump, piston or pressurized air.

It is to be understood that any ports of treatment chamber 10 (in FIG. 1), chamber 50 (in FIG. 2), bellows 100 (in FIG. 3), and chamber 150 (in FIG. 4) (hereinafter collectively referred to as the "treatment devices") may be sealed in a known manner (e.g., luer locks, o-ring based connectors, or threaded plugs) so as to create a sealed treatment device free from contamination. The sealed treatment devices may be used to sterilize, store, and ship tendon and ligament constructs or other protheses. In particular, prior to placing a sealed treatment device into the systems of FIGS. 1–4, a construct 20 which is secured within the treatment device may be sterilized by some chemical means such as ethylene oxide or peracetic acid, radiation means such as an electron beam or gamma rays, or by steam sterilization. Sealed treatment devices, containing the sterilized tendon or ligament support material, may then be placed back into the systems of FIGS. 1–4 for seeding and culturing and unsealed without contaminating the system or the tissue construct. Alternatively, the system may be aseptically assembled after sterilization if it is necessary or desirable to use different means to sterilize the treatment devices and the tissue construct.

Seeding and culturing of the constructs in the systems disclosed in FIGS. 1–4 is generally accomplished by known techniques, with the added benefits and advantages gained from the stress placed upon the construct during seeding or growth steps. Examples of suitable seeding and culturing methods for the growth of three-dimensional tissue cultures are disclosed in U.S. application Ser. No. 08/463,566, entitled "Three-Dimensional Cartilage Cultures" and filed on Jun. 5, 1995, and U.S. Pat. No. 5,266,480, both of which are incorporated herein by reference. The techniques described in this application and U.S. Patent for establishing a three-dimensional construct, inoculating the construct with the desired cells, and maintaining the culture may be readily adapted by a person of ordinary skill in the art for use with the present invention.

Once construct 20 has reached the desired level of cell density, a preservative may then be pumped into the treatment device. Once the device is filled with the preservative, any ports located on the device may be closed, again creating a sealed device which may then be used to store and/or ship the cultured and preserved construct. Preferably, the preservative is a cryo-preservative so that the construct may be frozen in the treatment device. In this manner, the sealed treatment devices may be used to sterilize, culture, store, and ship tendon and ligament constructs or other protheses.

Various embodiments of the invention have been described. The descriptions are intended to be illustrative, not limitative. Thus, it will be apparent to those skilled in the art that modifications may be made to the invention as described without departing from the scope of the claims set out below. For example, it will be recognized that the exemplary embodiments disclosed in conjunction with FIGS. 1–4 need not have both an inlet and an outlet port to apply an axial stress to the construct during culturing, but instead may have a plurality of ports, one port, or no ports. Likewise, if only a constant axial load on the tissue construct is desired, magnet 12 in FIG. 1 may, for example, be replaced with a non-magnetized dead weight. Similarly, an axial load can be placed on the constructs shown in FIGS. 2, 3, and 4 by varying the pressure external to the treatment chamber through, for example, the creation of a vacuum around the exterior of the chamber. This is advantageous as fluid access to the treatment chamber is not required.

Figure 5A:
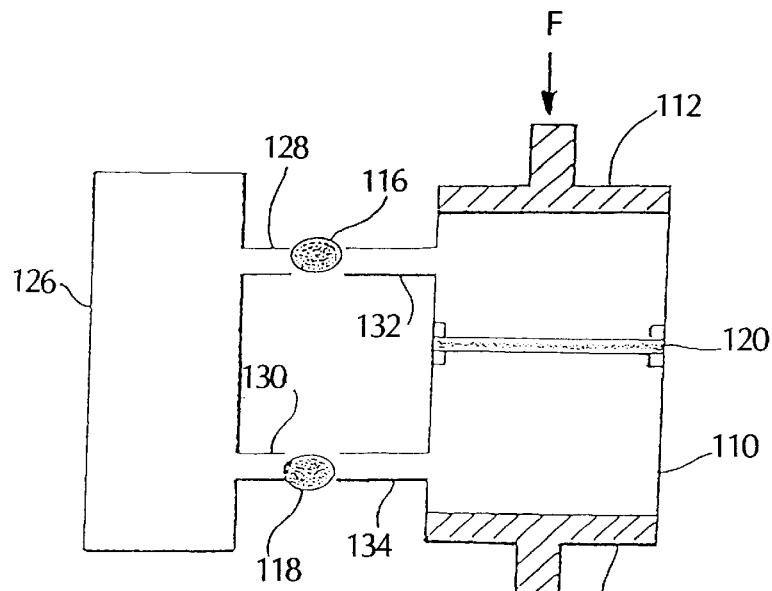
Figure 5B:
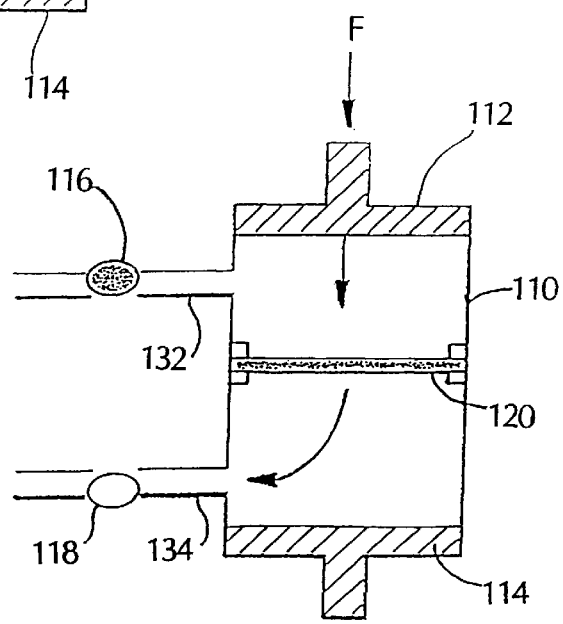
Figure 5C:
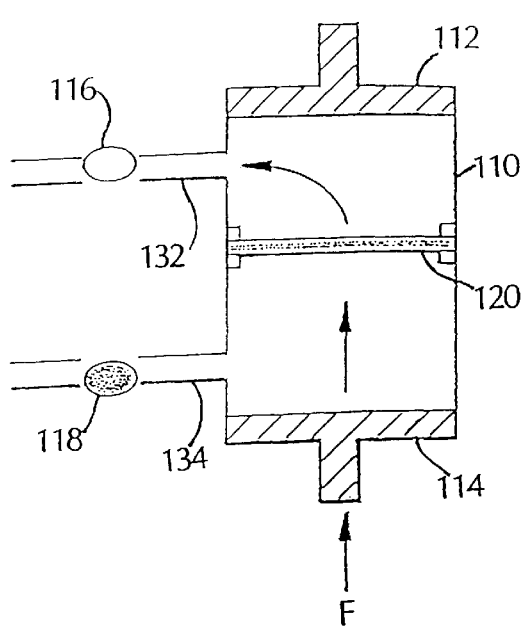

FIGS. 5A–5C disclose a system for sterilizing, seeding, culturing, storing, shipping, and testing cartilage constructs. According to a preferred embodiment of the invention, this system primarily comprises a treatment chamber 110, a pair of pistons 112 and 114, and a media reservoir 126 communicating with the treatment chamber.

Media reservoir 126 is used to store fluid for the system. Illustrative suitable reservoirs are the Gibco-BRL 1L media bag or any rigid container capable of sterilization. Reservoir 126 may include a one way sterile filter so as to provide a direct source of sterile gas to the fluid within the system or, alternatively, may include gas-permeable tubing or membranes comprised of a material such as silicone or Teflon so as to provide an indirect source of sterile gas to the system via diffusion. Examples of fluid which may be used in the system include, but are not limited to, sterilizing fluid, tanning fluid, fluid containing cells, or fluid containing a culture medium. It is to be understood that during testing, seeding, and culturing in a preferred embodiment, the fluid may be advantageously kept at human body temperature, and may be composed of a fluid which approximates the viscosity of human blood or other human bodily fluids.

The fluid contained in reservoir 126 is retrieved through fluid lines 128 and 130 into treatment chamber 110 through the actions of pistons 112 and 114, which, as is discussed below, control both the flow and pressure of the fluid within the system. Fluid lines 128 and 130, as well as all other fluid lines in the system, may be made of any type of stainless steel tubing or medical grade, sterilizable, durable, plastic tubing preferably comprised of a gas-permeable material such as silicone which is suitable for transporting the fluid in use.

Treatment chamber 110 preferably may be composed of any biocompatible, rigid material capable of being sterilized such as Teflon, polycarbonate, PVC, or stainless steel. Treatment chamber 110 may be a single piece of material or, as is discussed in more detail below, may be comprised of two sections which are secured and made leak proof through any standard means such as inner and outer threads, an o-ring seated in an annular groove, a clamp, or bonding agents. In order to view cartilage construct 120 within treatment chamber 110, a viewing port may be placed at any point on the chamber, or alternatively, the chamber may be made of an optically clear material such as polycarbonate or PVC. Ports 132 and 134 of treatment chamber 10 allow for the perfusion and/or circulation of fluid into and through the chamber. Ports 132 and 134 are also used to attach treatment chamber 110 to fluid lines 128 and 130 respectively. Valves 116 and 118 are disposed in fluid lines 128 and 130 to control flow therethrough. Valves 116 and 118 can be any valve that may be mechanically, pneumatically, and/or electronically opened and closed at a variety of intervals, and preferably non-invasive to minimize the potential for contamination of the cell culture medium.

As mentioned, treatment chamber 110 may be used to house a cartilage construct 120. Cartilage construct 120 may illustratively consist of any knitted, braided, woven, felted, or synthesized material that is bioresorbable and/or biocompatible, as well as any native cartilage material which will support appropriate cells. Treatment chamber 110 may be made any size so as to hold a cartilage construct 120 of any length or diameter. This is advantageous, as the system may be used to sterilize, seed, culture, store, ship, and test constructs of any size.

In a preferred embodiment of the present invention, construct 120 is secured within treatment chamber 110 so as to form a seal with the chamber around the periphery of the construct. Such a seal requires fluid flowing through chamber 110 to flow through construct 120, thus creating a pressure drop at the construct which creates an advantageous seeding and culturing environment. By controlling the flow through the chamber (by pumps, pistons or other means), the pressure drop is used to create alternating periods of higher and lower pressure acting on one or both sides of the construct. In an alternative embodiment in which less fluid flow through construct 120 is desired, construct 120 may be secured within chamber 110 in a manner which does not form a seal, and thus, which allows some fluid to flow around construct 120. Additionally, the necessary effects may be obtainable in a static chamber, without continuous flow. In such an embodiment, the construct is placed within a chamber containing a volume of desired media. The chamber is intermittently pressurized as is appropriate for the particular construct, for example by application of a piston or other means. The construct is thus exposed to alternating higher and lower pressures which tends to cause media to move in and out of the porous construct structure.

As mentioned, pistons 112 and 114 control both the flow and pressure of the fluid within treatment chamber 110. Pistons 112 and 114 are configured and dimensioned so as to create a hermetically sealed chamber 110. Force may be applied to pistons 112 and 114 (as shown by the arrows labeled F) by any well known means, such as an electrically-driven rotating cam, an electromechanical or pneumatic displacement device, or an electrically or pneumatically-driven lever arm. It is to be understood that the force applied to pistons 112 and 114 may be varied so as to provide varying pressure within treatment chamber 110 during use. This is advantageous as the ideal pressure to be applied to the construct will vary with time due to the increasing density of the construct during seeding and culturing. Moreover, the ideal pressure to be applied necessarily depends from the outset on the original thickness of the construct, and may thus vary from treatment to treatment.

FIGS. 5B and 5C particularly point out and illustrate the preferred fluid flow during use. This illustrated fluid flow is preferred for constructs of exceptional thickness or density, especially where avoidance of "sidedness" or a gradient in construct 120 is critical. FIG. 5B shows treatment chamber 110 when valve 116 is closed and a force is applied to piston 112. When piston 112 is moved towards construct 120 so as to shrink the volume of the chamber, all fluid is forced through the construct (as shown by the arrows) and out port 134.

However, as shown in FIG. 5C, once force is applied to piston 114 and valve 118 is closed, fluid is then forced in an opposite direction through construct 120 (as shown by the arrows) and out through open valve 116. Thus, in a preferred embodiment, the piston and valve positions are coordinated such that fluid is forced through construct 120 bidirectionally.

However, it is to be understood that pistons 112 and 114 may be actuated in any order and at any interval. Thus, pistons 112 and 114 may be actuated in an alternating fashion at some predetermined interval, or alternatively, one piston may be actuated for a predetermined period of time followed by actuation of the other piston for a preferably similar period of time. Likewise, both pistons may be actuated simultaneously to simulate intermittent cartilage pressurization without fluid flow similar to that found in the human body.

In this manner, periodic fluid flow and pressurization in treatment chamber 110 is accomplished which resembles the physiological conditions typically encountered by articular cartilage in the human body. These conditions are advantageous as they improve the flow of nutrients to and removal of waste products from cells embedded in the construct. These conditions are also advantageous as they can be detected by living cells attached to construct 120, thus causing the cells to align and configure themselves in a manner more likely to tolerate the physiological conditions found in the human body.

Figure 6A:
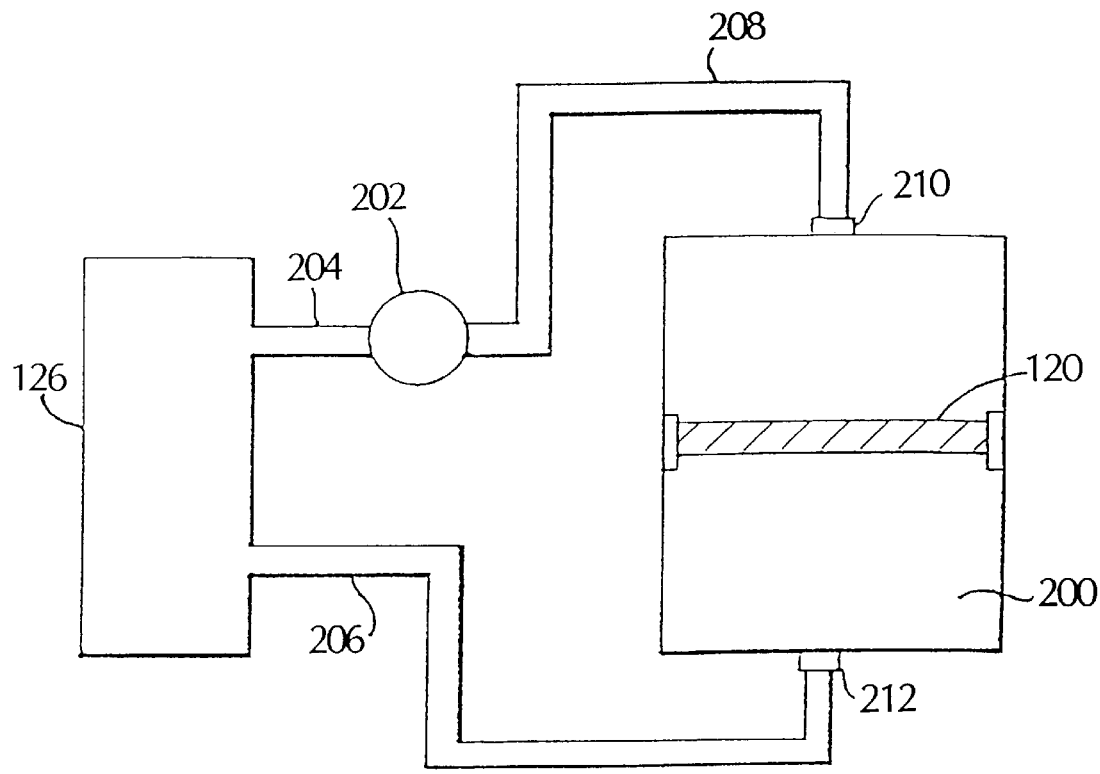
FIGS. 6A–6B illustrate an apparatus according to the present invention for sterilizing, seeding, culturing, storing, shipping, and testing a cartilage prosthesis, in which a pump is utilized.
Figure 6B:
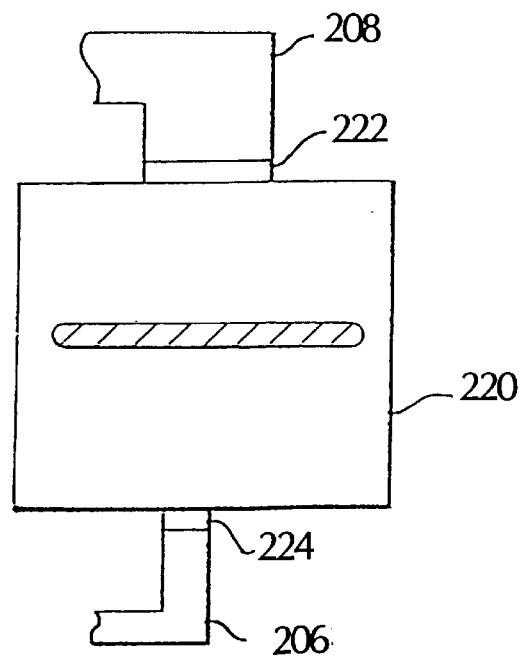

FIGS. 6A–6B disclose an alternative embodiment of a system for sterilizing, seeding, culturing, storing, shipping, and testing cartilage constructs. According to a preferred embodiment of the invention, shown in FIG. 6A, this system primarily comprises a treatment chamber 200, a pump 202, and a media reservoir 126 communicating with the treatment chamber.

Media reservoir 126, and the fluids which it may contain are the same as those disclosed in conjunction with FIGS. 5A–5C. The fluid contained in reservoir 126 may be retrieved through fluid lines 204 and 206 into treatment chamber 200 through the action of pump 202, which, as is discussed below, controls both the flow and pressure of the fluid within the system. Fluid lines 204 and 206, as well as all other fluid lines in the system, may illustratively be made of any type of stainless steel tubing or medical grade, sterilizable, durable tubing preferably comprised of a gas-permeable material such as silicone which is suitable for transporting the fluid in use.

Treatment chamber 200 preferably may be composed of any biocompatible, rigid material capable of being sterilized such as Teflon, polycarbonate, PVC, or stainless steel. Like treatment chamber 110 disclosed in FIGS. 5A–5C, treatment chamber 200 may be a single piece of material or, as is discussed in more detail below, may be comprised of two sections which are secured and made leak proof through any standard means such as inner and outer threads, an o-ring seated in an annular groove, a clamp, or bonding agents. In order to view cartilage constructs within treatment chamber 200, a viewing port may be placed at any point on the chamber, or alternatively, the chamber may be made of an optically clear material such as polycarbonate or PVC. Ports 210 and 212 of treatment chamber 200 allow for the perfusion and/or circulation of fluid into and through the chamber. Ports 210 and 212 are also used to attach treatment chamber 200 to fluid lines 208 and 212 respectively.

Treatment chamber 200 may be used to house cartilage construct 120. Treatment chamber 200 may be made any size so as to hold a cartilage construct 120 of any length or diameter. This is advantageous, as the system may be used to sterilize, seed, culture, store, ship, and test constructs of any size.

As in the embodiment disclosed in FIGS. 5A–5C, construct 120 may preferably be secured within treatment chamber 200 in a manner which forms a seal around the periphery of the construct. Thus, treatment chamber 200 may contain ferrules or flanges which allow the sections of a two-piece chamber to be secured together by clamp. The connection between the sections may also be made leak proof by a gasket or an o-ring, which can be seated in the annular grooves of the flanges found in each section. Construct 120 may be made so as to fit securely in between the sections of a two-piece treatment chamber 200 so as to hold the construct 120 firmly in place in chamber 200 and create a seal during treatment. Construct 120 may also be secured in place in between two screens or other matrix members which may also be secured in place between the sections so as to create a seal. The screens or matrix members may also be attached by any mechanical means within chamber 200. However, one skilled in the art will understand that any structure which allows for retention of the construct 120 in chamber 200 may be used. Construct 120 may be secured in place between the two sections or so as to form a seal which allows for a pressure drop at construct 120 during treatment. Alternatively, construct 120 may be secured in place in between two screens or matrix members which may be secured in place between the threaded sections.

As mentioned, pump 202 controls both the flow and pressure of the fluid within treatment chamber 200. Pump 202 may preferably be any reversible pump capable of providing bidirectional pulsatile or continuous pressure fluid flow in the system. Examples of such pumps include but are not limited to low flow pumps, invasive pumps such as a lobe-type pump, or non-invasive pumps such as a peristaltic pump. Alternatively, pump 202 may be comprised of two one way pumps situated so as to provide bi-directional fluid flow within the system.

Thus, illustratively, when pump 202 is operating so as to force fluid from reservoir 126 to fluid line 204, and subsequently from fluid line 208 into chamber 200, fluid is forced through the construct from port 210 to port 212. However, once pump 202 is operated so as to provide fluid flow in the opposite direction, fluid is then forced in an opposite direction through construct 120 from port 212 to port 210. Thus, in a preferred embodiment, pump 202 is operated such that fluid is forced through construct 120 bidirectionally.

It is to be understood that the pressure from pump 202 may be varied during use so as to provide varying pressure within treatment chamber 200. Moreover, it is to be understood that pump 202 may be operated bidirectionally in any manner and at any interval. Thus, pump 202 may be operated so as to provide bidirectional fluid flow in an alternating fashion at some predetermined interval. Alternatively, pump 202 may provide fluid flow in one direction for a predetermined period of time followed by fluid flow in the opposite direction for a preferably similar period of time. Moreover, it is to be understood that, alternatively, one skilled in the art could devise a suitable valving system (e.g., through the use of a rotating valve) that could also provide chamber 200 with a bidirectional fluid flow across construct 120.

Alternatively, treatment chamber 220 shown in FIG. 6B may be used in conjunction with pump 202. In this embodiment, port 222 is larger than orifice 224 of treatment chamber 220. In addition, in this embodiment pump 202 would preferably only pump fluid in one direction through chamber 220, that is from fluid line 226 and port 222 to orifice 224 and fluid line 228, so that a pressure drop is created at orifice 224 and the pressure within chamber 220 is elevated. In this manner, construct 120, which may be either free floating within chamber 220 as shown, loosely secured in the middle of chamber 220, or secured so as to create a seal or a partial seal within the chamber, will experience periodic fluid flow and pressurization in treatment chamber 220 which resembles the physiological conditions typically encountered by articular cartilage in the human body.

Figure 7A:
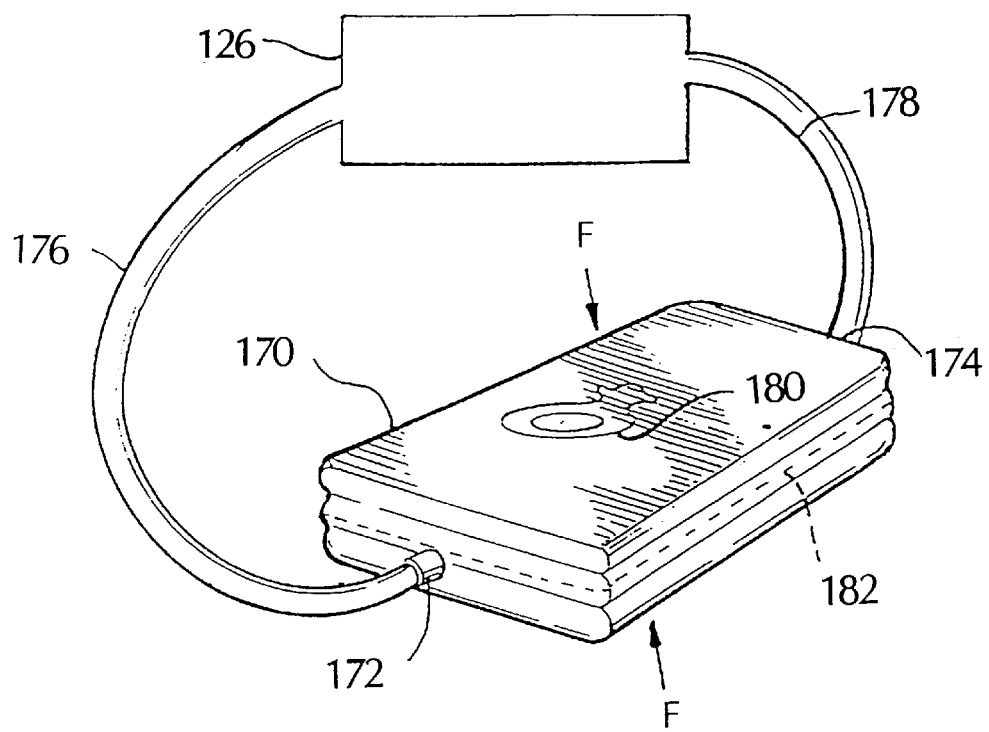
Figure 7B:
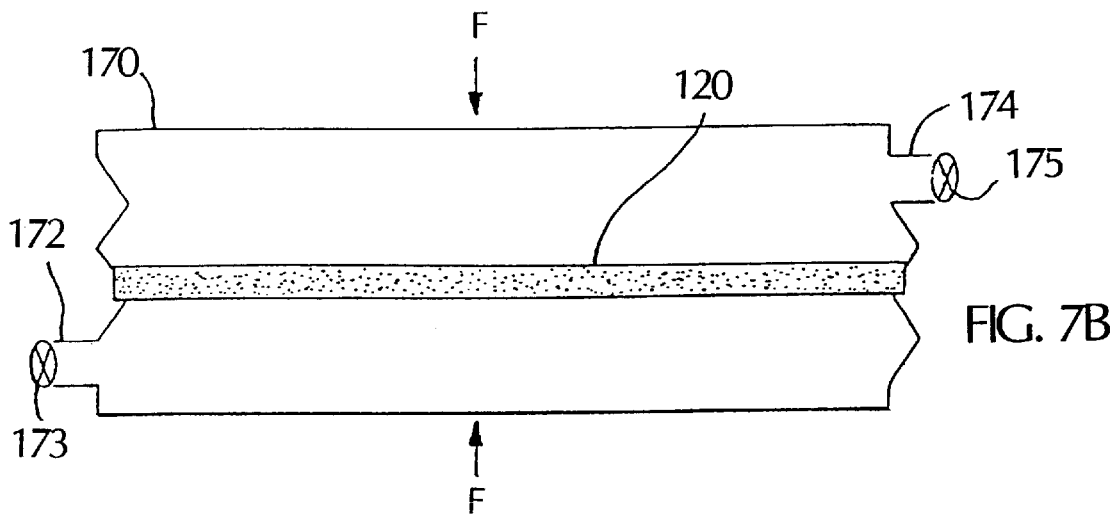

FIGS. 7A–7B disclose an alternative embodiment of the invention for sterilizing, seeding, culturing, storing, shipping, and testing cartilage constructs. According to this alternative embodiment of the invention, the system primarily comprises a bellows 170 and a fluid reservoir 126.

Fluid reservoir 126 and the fluids which it may contain are described in detail in conjunction with FIGS. 5A–5C. In the system of FIGS. 7A–7B, the fluid contained in reservoir 126 is retrieved through fluid line 176 by the action of bellows 170. In a preferred embodiment, bellows 170 may be comprised of a hard-sided blow molded collapsible bellows cassette. However, one skilled in the art will understand that other types of bellows which include at least one rigid surface and a flexible edge may be used. Bellows 170 may also include an external pull ring 180 for easy expansion, and may further include a sealable slit 182 along the collapsible side wall so as to place a construct 120 within the bellows for treatment. However, it is to be understood that sealable slit 182 may be placed at any location on bellows 170.

Cartilage construct 120 may be mounted in the center of bellows 170 for treatment. As in the previously discussed embodiments, construct 120 may preferably be mounted within bellows 170 so as to form a sealed barrier in the bellows. Methods of mounting one or more constructs 120 in bellows 170 are shown and described U.S. patent application Ser. No. 08/486,185, which is incorporated herein by reference. Briefly, construct 120 may be attached to a frame or other support structure by any means such as sutures, staples, c-clips, or may be sandwiched between two opposable interlocking frames. Frames may be comprised of any material such as plastic or elastomeric polymers including, but not limited to, fluorinated polymers, polycarbonate, ester- or vinyl-based polymers and polyolefin polymers, and may be attached or anchored within bellows 170 through pins or other mechanical means which preferably allow for the formation of a tight seal between the frame and the walls of the bellows. However, one skilled in the art will understand that any structure which allows for the retention of construct 120 within bellows 170 may be used. For example, as mentioned in conjunction with FIGS. 5A–5C, in a lesser preferred embodiment, construct 120 may be attached in a manner that does not form a seal, and thus, which allows some fluid to flow around and not through construct 120.

As shown by the arrows in FIGS. 7A and 7B, a mechanical force may be applied to bellows 170 so as to apply pressure to construct 120 and force fluid through the bellows. One skilled in the art will understand that any type of mechanical force, such as a an electromechanical or pneumatic displacement device or an electrically or pneumatically-driven lever arm, may be used to place a force on the bellows. In a preferred embodiment of the invention, bellows 170 is alternately expanded and contracted so as to force fluid through the bellows as well as through construct 120 mounted within the bellows. Expanding and contracting bellows 170 also acts to place a varying pressure on construct 120. Ports 172 and 174 allow for the perfusion and/or circulation of fluid into and through bellows 170. Ports 172 and 174 are also used to attach bellows 170 to fluid lines 176 and 178 respectively. Fluid line 178 connects bellows 170 back to reservoir 126 so as to create a closed system.

Ports 172 and 174 preferably may include valves 173 and 175 as shown in FIG. 7B so as to assure that fluid may be forced to flow bidirectionally through bellows 170. Valves 173 and 175 can be any valve that may be mechanically, pneumatically and/or electronically opened and closed at a variety of intervals, and preferably non-invasive to minimize the potential for contamination of the cell culture medium.

Thus, the opening and closing of valves 173 and 175 may be coordinated so that one valve is opened and one valve is closed when the bellows is expanded, and then, when the bellows is contracted, the opened valve is closed and the closed valve is opened. This may be followed on the next expansion and contraction of the bellows by the valves being opened and closed in an opposite manner so that fluid is forced in the opposite direction through bellows 170.

Illustratively, when bellows 170 is expanded by an outside force, fluid could be drawn from fluid reservoir 126 from opened valve 173 into bellows 170 until the bellows is filled with fluid and is in a fully expanded state. During expansion of bellows 170, closed valve 175 will ensure that no fluid is drawn from fluid line 178. Once a positive pressure is applied to bellows 170, the fluid contained in the bellows is forced through construct 120, out of the bellows, and through now opened valve 175 back to reservoir 126. When fluid is forced out of bellows 170, the now closed valve 173 located at port 172 will ensure that no fluid is forced back into fluid line 176. This may be followed on the next expansion and contraction of bellows 170 by the opening and closing of the valves in an opposite manner so that bidirectional fluid flow is created.

However, in a lesser preferred embodiment, simple check valves may be used at ports 172 and 174 so that a unidirectional fluid flow through bellows 170 may be instituted.

Thus, like the system of FIGS. 5A–5C, fluid flow and pressurization is accomplished during seeding, culturing, and testing which closely resembles the physiological conditions found in the human body.

Figure 8:
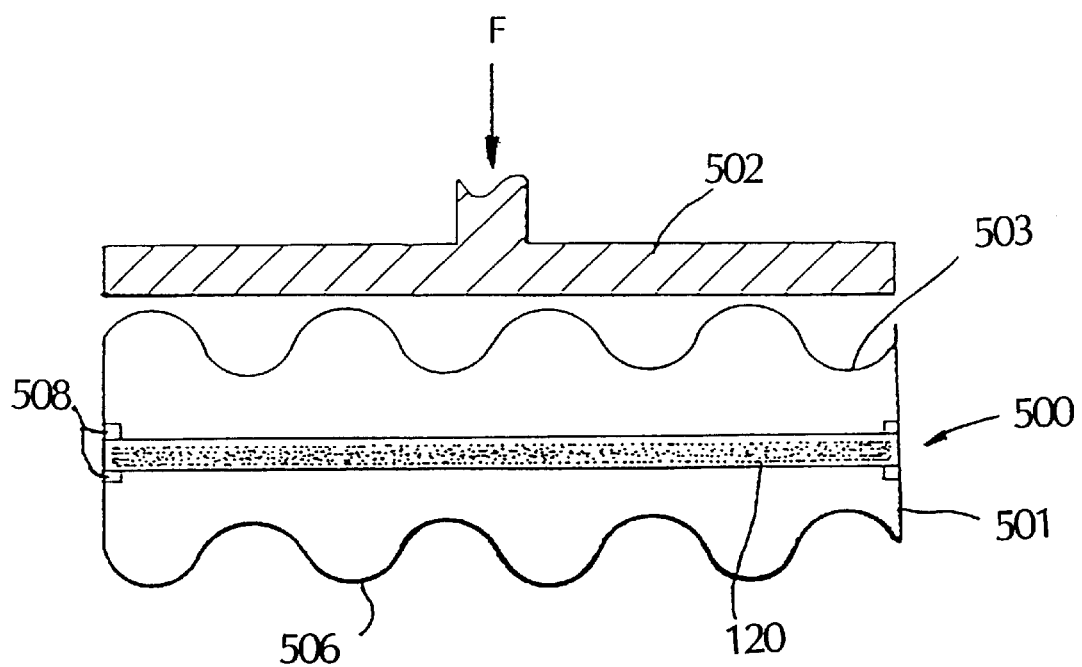
FIG. 8 illustrates another alternative exemplary embodiment of the present invention for sterilizing, seeding, culturing, storing, shipping, and testing a cartilage prosthesis in which a pressure plate is utilized.

FIG. 8 discloses yet another alternative embodiment of the invention for sterilizing, seeding, culturing, storing, shipping, and testing cartilage constructs. According to this alternative embodiment of the invention, the system primarily comprises a flexible treatment chamber 500 and at least one pressure plate 502.

Flexible treatment chamber 500 may be used to house any type of suitable fluid, such as those disclosed in conjunction with FIGS. 5A–5C, as well as cartilage construct 120. As shown in FIG. 4, chamber 500 may preferably be comprised of a rigid wall 101 and flexible covers 503 and 506. Rigid wall 501 illustratively may be circular or rectangular in shape. Moreover, cover 506 may be a rigid wall so that wall 501 and cover 506 form a rigid tray. Covers 503 and 506 may be comprised of any biocompatible flexible material, including, but not limited to, plastic or elastomeric polymers such as silicone, fluorinated polymers, ester- or vinyl-based polymers and polyolefin polymers, which preferably allow for the diffusion of gas from the environment into the chamber. Chamber 500 may also include one way inlet and outlet filters so as to provide a direct source of gas to the fluid within the system as well as to provide a method of removing gas from the system. As shown in FIG. 8, during seeding and culturing of construct 120 within treatment chamber 500, pressure plate 502 may be used to apply predetermined levels of pressure (as shown by the arrow labeled F) at predetermined intervals to the chamber and thus, to construct 120 within the chamber. One skilled in the art will understand that any type of mechanical means may be used to apply a force to pressure plate 502.

In an alternative embodiment, a second pressure plate 502 may be used to apply predetermined levels of pressure to the chamber through cover 506, and thus, from the opposite direction of the first pressure plate. Like the actuation of the pistons in FIGS. 5A–5C, in a preferred embodiment, the actuation of the two pressure plates may be coordinated such that fluid is forced through construct 120 bidirectionally.

However, it is to be understood that the two pressure plates 502 may be actuated in any order and at any interval. Thus, the pressure plates may be actuated in an alternating fashion at some predetermined interval, or alternatively, one pressure plate may be actuated for a predetermined period of time followed by actuation of the other pressure plate for a preferably similar period of time. Likewise, both pressure plates may be actuated simultaneously to simulate intermittent cartilage pressurization without fluid flow as is found in the human body.

In this manner, periodic fluid flow and pressurization in treatment chamber 500 is accomplished which resembles the physiological conditions typically encountered by articular cartilage in the human body. These conditions are advantageous as they improve the flow of nutrients to and removal of waste products from cells embedded in the construct. These conditions are also advantageous as they can be detected by living cells attached to construct 120, thus causing the cells to align and configure themselves in a manner more likely to tolerate the physiological conditions found in the human body.

FIG. 8 also discloses a cartilage mount 508 for mounting construct 120 in the center of chamber 500. Various embodiments of cartilage mount 508 and methods of securing construct 120 are disclosed in U.S. patent application Ser. No. 08/486,185.

In an alternative embodiment, a media reservoir may be connected to chamber 500 in the same manner as media reservoir 126 is connected to bellows 170 in FIG. 7A. Thus, in this alternative embodiment, chamber 500 would include two ports having valves on the opposite sides of the preferable seal created by construct 120 secured within chamber 500. These valves may be operated like those disclosed in conjunction with FIGS. 7A–7B so that bidirectional fluid flow may be created through construct 120.

During treatment, it may be desirable to periodically de-gas chamber 500 so as to improve the effectiveness of the system disclosed in FIG. 8. De-gassing may be accomplished by a variety of methods, such as raising chamber 500 in a vertical orientation and forcing the gas out through a sterile filter located at a predetermined position on the chamber. Finally, like the system disclosed in FIGS. 7A–7B, this system is more amenable to operating at lower pressures than that of the system disclosed in FIGS. 5A–5C.

Figure 9A:
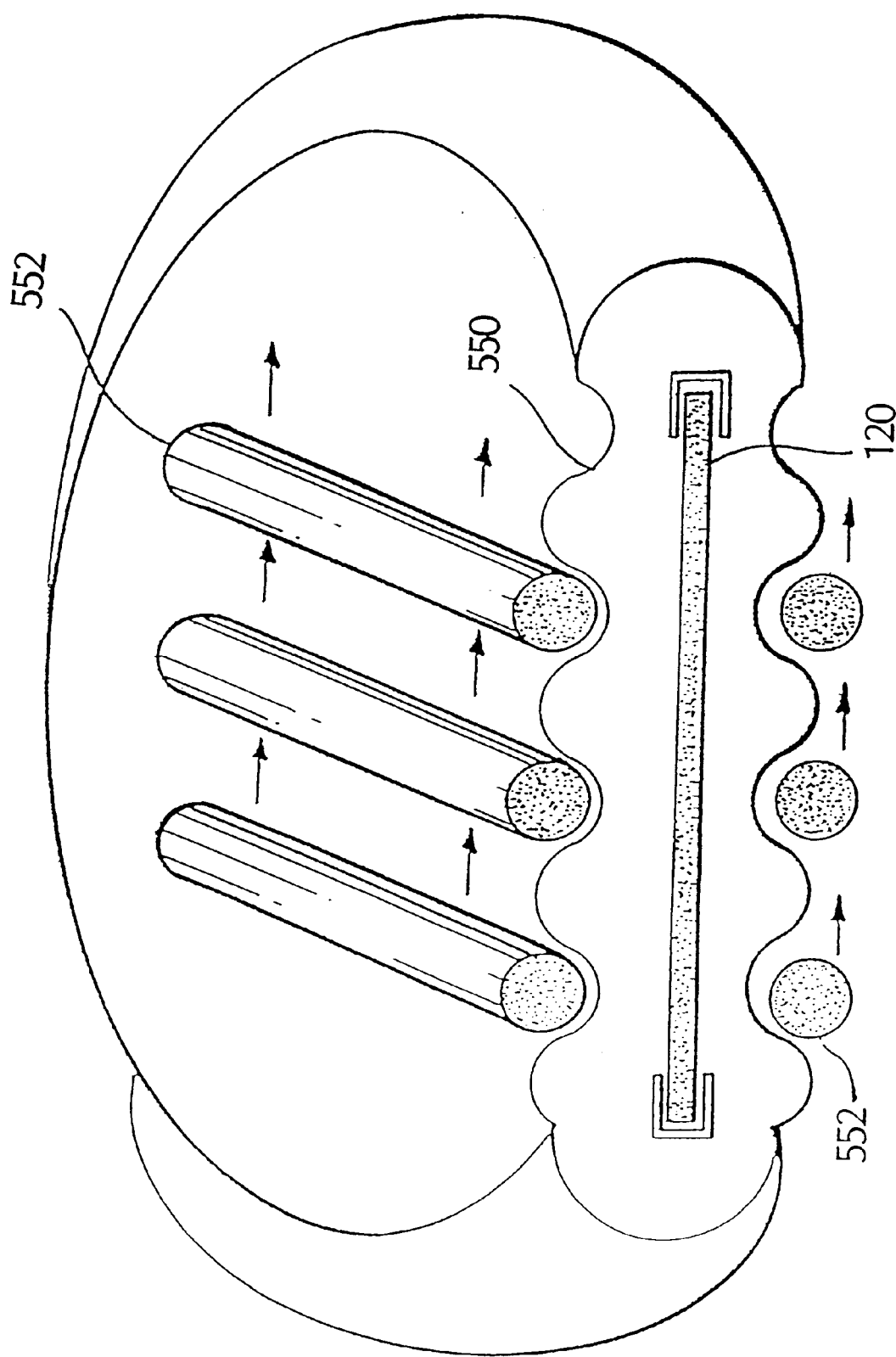
FIGS. 9A–9C illustrate yet another alternative exemplary embodiment of an apparatus according to the present invention for sterilizing, seeding, culturing, storing, shipping, and testing a prosthesis, in which rollers are utilized.
Figure 9B:
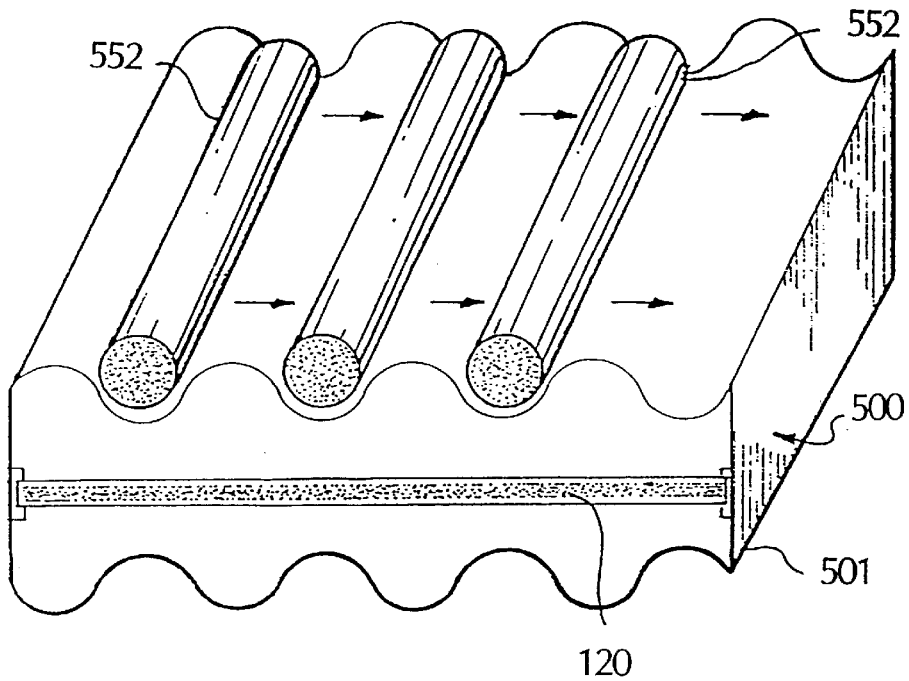
Figure 9C:
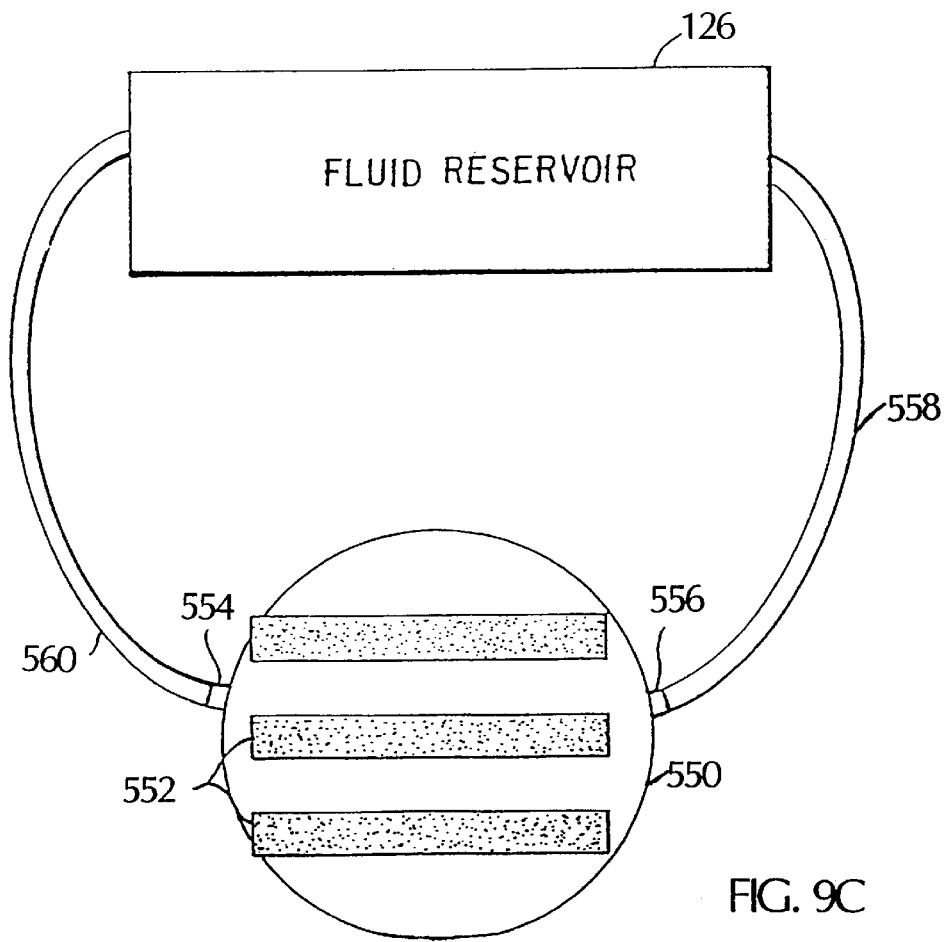

FIGS. 9A–9C disclose yet another alternative embodiment of the invention for sterilizing, seeding, culturing, storing, shipping, and testing cartilage constructs. According to this alternative embodiment of the invention, the system primarily comprises a flexible treatment chamber and at least one roller 552.

Flexible treatment chamber 550 shown in FIG. 9A may be used to house any type of fluid, such as those disclosed in conjunction with FIGS. 5A–5C, as well as a cartilage construct 120. Chamber 550 may preferably be comprised of any biocompatible flexible, gas-permeable material, including, but not limited to, plastic or elastomeric polymers such as silicone, fluorinated polymers, ester- or vinyl-based polymers and polyolefin polymers, which also allows for the diffusion of gas from the environment into the chamber. Chamber 550 may be either sealed so as to create a closed chamber or may include valves, such as timed or check valves, which as shown in FIG. 9C, further link chamber 550 to a media reservoir 126 through lines 558 and 560. Chamber 550 may also include one way inlet and outlet filters so as to provide a direct source of gas to the fluid within the system, and may also include a port for adding or removing fluid media from the chamber.

A construct 120 may be secured in chamber 550 in any manner disclosed above so as to create a seal within chamber 550. If construct 120 is relatively thin, it may not be necessary to positively force flow through the porous structure of the construct. In such a case, high pressures or a peripheral seal may not be required. This is because with a relatively thin construct, convection of the fluid around the construct may provide adequate fluid communication with the cells for seeding, culturing and waste removal, rather than fluid flow through the construct.

As shown in FIG. 9A, during seeding and culturing of construct 120 within treatment chamber 550, rollers 552 may be used to apply pressure to opposite sides of the chamber and thus, to construct 120 within the chamber. Although three rollers are disclosed in FIG. 9A, any number of rollers could be used to apply pressure depending on the size of the construct and the performance of the roller system. As is the case with the system disclosed in FIG. 8, any level of pressure may be applied at any interval. One skilled in the art will understand that any type of mechanical means may be used to move rollers 552 across the surface of chamber 550. In this embodiment, valves may be situated at ends 554 and 556 (shown in FIG. 9C) in a manner which allows for fluid flow in only one direction or bidirectionally through chamber 550 and through construct 120. In this manner, whether or not a fluid reservoir is utilized, fluid flow is created through construct 120 within chamber 550, creating a dynamic seeding and culturing environment.

Alternatively, as shown in FIG. 9B, rollers 552 may be applied to chamber 500 disclosed in FIG. 8. As mentioned, although chamber 500 may comprise a sealed chamber, in an alternative embodiment, chamber 500 may include valves so as to connect the chamber to media reservoir 126.

It is to be understood that any ports of treatment chamber 110 (in FIGS. 5A–5C), chamber 200 (in FIG. 6A), chamber 220 (in FIG. 6B), bellows 170 (in FIGS. 7A–7B), chamber 500 (in FIGS. 8 and 9B), or chamber 550 (in FIG. 9A) (hereinafter collectively referred to as the "treatment devices") may be sealed in a known manner (e.g., luer locks, o-ring based connectors, or threaded plugs) so as to create a sealed treatment device free from contamination. The sealed treatment devices may be used to sterilize, store, and ship cartilage constructs or other protheses. In particular, prior to placing a sealed treatment device into the systems of FIGS. 5–9, a construct 120 which is secured within the treatment device may be sterilized by some chemical means such as ethylene oxide or peracetic acid, radiation means such as an electron beam or gamma rays, or by steam sterilization. Sealed treatment devices, containing the sterilized cartilage support material, may then be placed back into the systems of FIGS. 5–9 for seeding and culturing and unsealed without contaminating the system or the cartilage construct. Alternatively, the system may be aseptically assembled after sterilization if it is necessary or desirable to use different means to sterilize the treatment devices and the cartilage construct.

Seeding and culturing of the constructs in the systems disclosed in FIGS. 5–9 is generally accomplished by known techniques, with the added benefits and advantages gained from the stress placed upon the construct during seeding or growth steps. Examples of suitable seeding and culturing methods for the growth of three-dimensional cartilage cultures are disclosed in U.S. Pat. No. 5,902,741, which is incorporated herein by reference. The techniques described in this application for establishing a three-dimensional cartilage construct, inoculating the construct with the desired cells, and maintaining the culture may be readily adapted by a person of ordinary skill in the art for use with the present invention.

Further details of the apparatus according to the present invention for sterilizing, seeding, culturing, storing, shipping, and testing cartilage tissue constructs are found in U.S. patent application Ser. No. 08/486,185, which is incorporated herein by reference.

Figure 10:
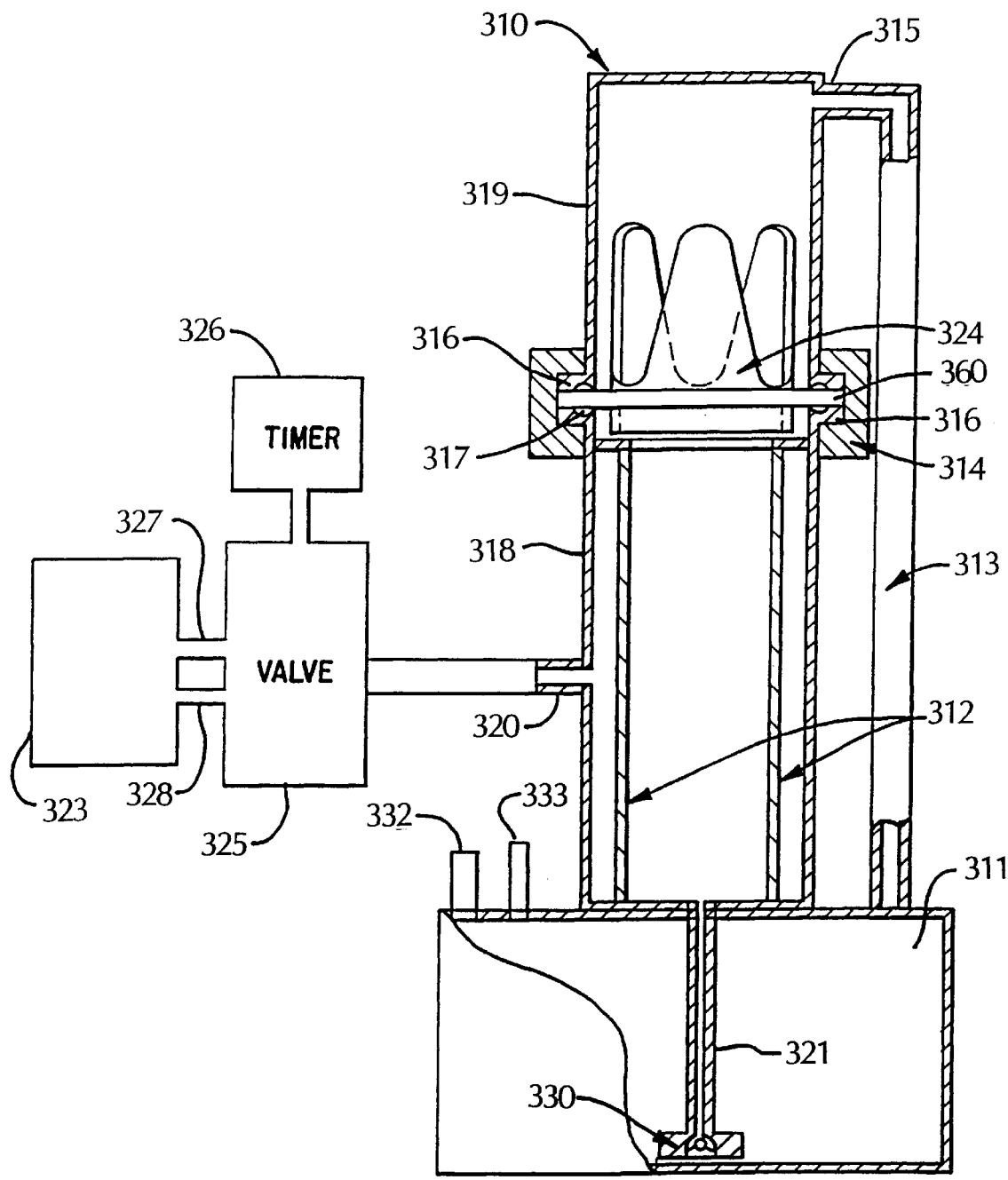
FIG. 10 illustrates an apparatus according to the present invention for sterilizing, seeding, culturing, storing, shipping, and testing a heart valve prosthesis.

FIG. 10 discloses a system for sterilizing, seeding, culturing, storing, shipping, and testing heart valves. According to a preferred embodiment of the invention, this system primarily comprises a valve bioreactor 310, an alternating pressure source 323, a valve 325, and a timer 326.

Bioreactor 310 contains a fluid reservoir 311 for storing fluid for the system. Examples of fluid which may be used in the system include, but are not limited to, sterilizing fluid, tanning fluid, fluid containing cells, or fluid containing a culture medium. It is to be understood that during testing, seeding, and culturing in a preferred embodiment, the fluid may be advantageously kept at human body temperature, and may be composed of a fluid which approximates the viscosity of human blood. One illustrative example of a solution which approximates the viscosity of blood is saline with glycerol. In a preferred embodiment, fluid reservoir 311 may include an aspiration port 333 for removing or replenishing the fluid contained in the system.

During use, the fluid contained in reservoir 311 is retrieved through check valve 330 and fluid line 321 by the action of pneumatic pressure chamber 318 and bladder 312, which may be comprised of any suitable elastomeric material. An illustrative suitable bladder is the Cutter/Miles double-valved hand activated blood pump. Bladder 312, which is contained in chamber 318, forces fluid from reservoir 311 through a heart valve mounted on valve holder 324 by being alternately compressed and expanded by alternating pressure source 323 in conjunction with valve 325 and timer 326. Alternating pressure source 323 preferably may be any standard pump capable of providing both positive pressure and negative (or vacuum) pressure, such as a piston or diaphragm pump. Valve 325 accepts the positive pressure and negative pressure from pump 323 through lines 327 and 328, respectively. Due to signals from timer 326, valve 325 causes alternating positive and negative pressure to be applied to bladder 312 from line 320. Valve 325 may be any type of inline valve capable of directing and regulating multiple lines. One such valve is the MAC 45S, model 45A-AA1-DAAA-1BA.

As shown in FIG. 10, once the fluid is forced through the heart valve, the fluid exits chamber 319 through outlet 315 and is returned to reservoir 311 through return line 313. Return line 313 may be made of any type of medical grade tubing suitable for transporting fluid. Return line 313 may be made of a substance which allows for the diffusion of gas. This is beneficial because human cells placed in the system need a minimum concentration of carbon dioxide to survive. Return line 313 may also be made longer than necessary for fluid connection purposes so as to allow for a higher gas diffusion rate by providing more surface area. However, in a preferred embodiment of the invention, return line 313 is made of a noncompliant substance such as polyurethane which can withstand pressure within the system.

A gas port 332 supplying the appropriate mixture of gas may also be connected to the apparatus to provide a direct source of gas to the system. If gas port 332 is connected to the system, a one way filter can be placed at the connection between gas port 332 and the apparatus to eliminate any airborne contaminants.

Chambers 318 and 319, as well as fluid reservoir 311, of bioreactor 310 may be composed of any rigid, biocompatible material capable of being sterilized such as Teflon, PVC, polycarbonate, or stainless steel. It is to be further understood that chambers 318 and 319 also contain ferrules or flanges 316 which allow the chambers to be secured together by clamp 314. Clamp 314 may be any suitable clamp such as a sanitary clamp. Alternatively, chambers 318 and 319 may be threaded together. Further details of the methods of connecting chambers 318, 319 and securing heart valve 324 are disclosed in U.S. Pat. No. 5,846,828, which is incorporated herein by reference in its entirety.

Figure 11:
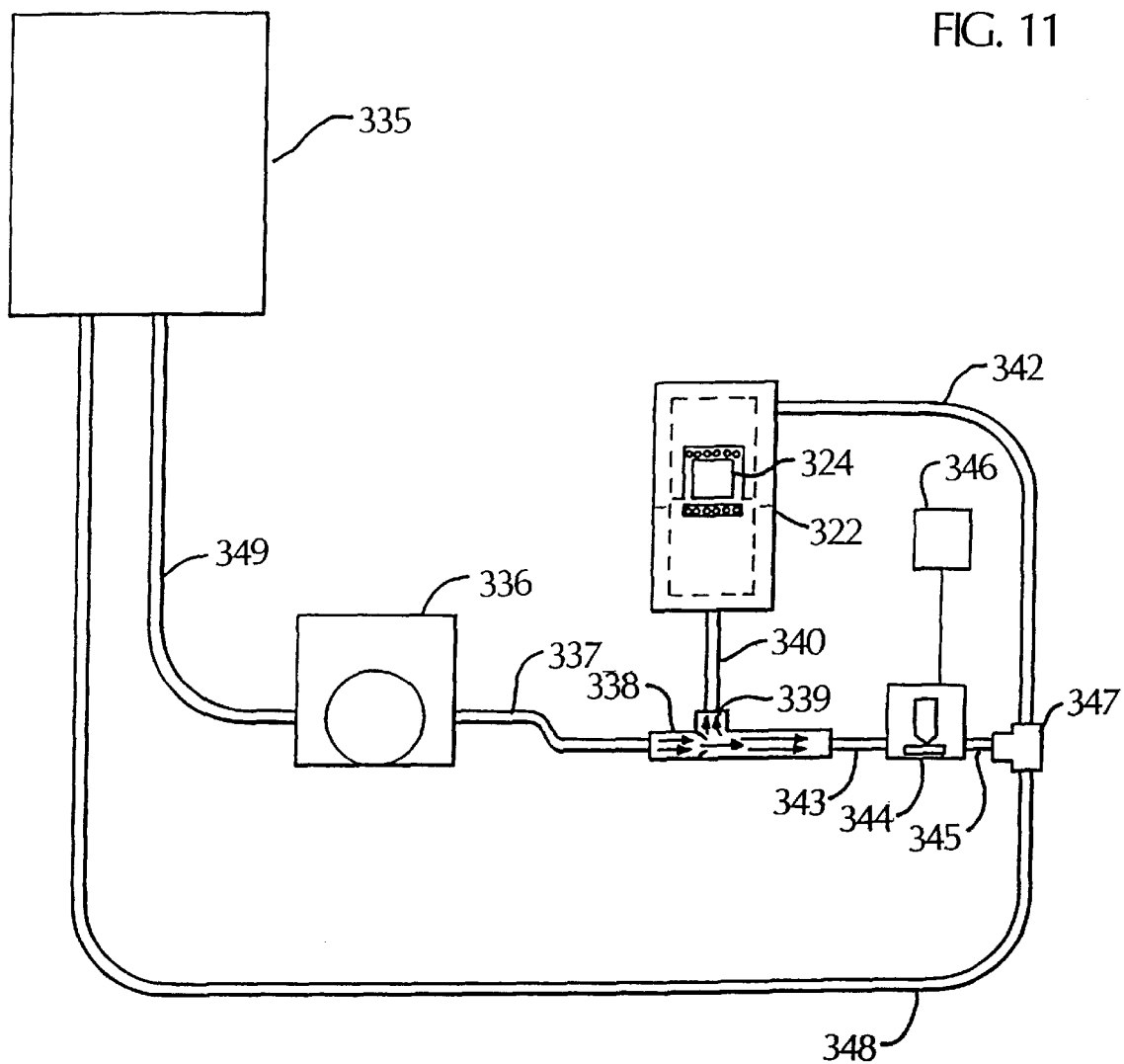
FIG. 11 illustrates an alternative exemplary embodiment of an apparatus according to the present invention for sterilizing, seeding, culturing, storing, shipping, and testing a heart valve prosthesis.

FIG. 11 discloses an alternative system for sterilizing, seeding, culturing, storing, shipping, and testing heart valves. According to this embodiment of the invention, the system primarily comprises a fluid reservoir 335, a pump 336, a venturi tube 338, a treatment chamber 322, and a pincher valve 344 connected to a timer 346.

Fluid reservoir 335, like fluid reservoir 311 in FIG. 10, is used to store fluid for the system (two illustrative suitable reservoirs would be the Gibco-BRL 1L media bag and any type of rigid, sterilizable container). Examples of fluid which may be used in the system are the same as those discussed in detail in conjunction with FIG. 10 above. In FIG. 11, the fluid contained in reservoir 335 is retrieved through fluid line 349 by pump 336. Fluid line 349, as well as all other fluid lines in the system, may be made of any type of medical grade tubing suitable for transporting the fluid in use. However, the fluid lines may preferably be made of a substance such as silicone which allows for the diffusion of gas. Pump 336 may be preferably any fluid pump which can achieve the flow rate found in the human heart. One such pump is the Masterflex L/S Digital Drive peristaltic pump manufactured by Cole-Palmer, although one skilled in the art could select from a variety of commercially available pumps. Pump 336 propels the fluid from reservoir 335 to venturi tube 338 through fluid line 337.

Venturi tube 338 may be any type of constriction mechanism which causes a drop in pressure as fluid flows through it. Side port 339 is located in the side of the venturi tube, immediately downstream from the constriction. The drop in pressure through venturi tube 338 is used to draw fluid from fluid line 340 through side port 339 and into the flow stream from fluid line 337 to fluid line 343. One illustrative example of a suitable venturi tube is the Nalgene Vacuum Pump with a maximum vacuum of 28.5 in.Hg. Through use of venturi tube 338, and as further discussed below, cycling and pulsatile bi-directional fluid flow through treatment chamber 322 may be achieved.

Fluid flows from venturi tube 338 to pincher valve 344 through fluid line 343. Pincher valve 344 is connected to timer 46 which may be used to variably open and close pincher valve 344. Pincher valve 344 may be any type of valve which can be variably opened and closed according to a desired program. (e.g., the Solenoid Valve manufactured by BioChem Valve Corp).

Treatment chamber 322 is connected to side port 339 of venturi tube 338 by fluid line 340. Treatment chamber 322 houses valve holder 324, which in turn holds the heart valve firmly in place within the chamber.

The outlet of chamber 322 and the outlet of pincher valve 344 are connected to line tee 347 by fluid lines 342 and 345, respectively. Line tee 347 connects the system back to fluid reservoir 335 through fluid line 348.

By connecting the system in this manner, a variable cycling and pulsatile flow may be achieved through treatment chamber 322. Specifically, when pincher valve 344 is closed due to signals from timer 346, fluid flows into venturi tube 338, out the side port 339, and through treatment chamber 322 from fluid line 340 to fluid line 342. However, when pincher valve 344 is opened due to signals from timer 346, venturi tube 338 draws fluid into side port 339 from treatment chamber 322, causing fluid to flow in a direction from fluid line 342 to fluid line 340. Thus, by altering the pressure differential across the heart valve, a variable cycling and pulsatile fluid flow closely resembling the physiological conditions of the human heart may be advantageously achieved in the system.

Seeding and culturing of the heart valve in chambers 319 and 322 is generally accomplished by known techniques, with the added benefits and advantages gained from the cycling and pulsatile fluid flow achievable with the systems according to the present invention. Examples of suitable seeding and culturing methods for the growth of three-dimensional cell cultures are disclosed in U.S. Pat. No. 5,266,480, which is incorporated herein by reference. The techniques described in U.S. Pat. No. 5,266,480 for establishing a three-dimensional matrix, inoculating the matrix with the desired cells, and maintaining the culture may be readily adapted by a person of ordinary skill in the art for use with the present invention.

Once the heart valve culture has reached the desired level of cell density, a preservative may then be pumped into chambers 319 and 322. Once chambers 319 and 322 are filled with the preservative, they may again be sealed so as to be used to store and/or ship the cultured and preserved heart valve. Preferably, the preservative is a cryo-preservative so that the valve may be frozen in the chambers. In this manner, sealed chambers 319 and 322 may be used to sterilize, culture, store, and ship heart valves or other protheses.

Further details of the apparatus according to the present invention for sterilizing, seeding, culturing, storing, shipping, and testing a heart valve prosthesis are found in U.S. Pat. No. 5,846,828, which is incorporated herein by reference.

Figure 12:
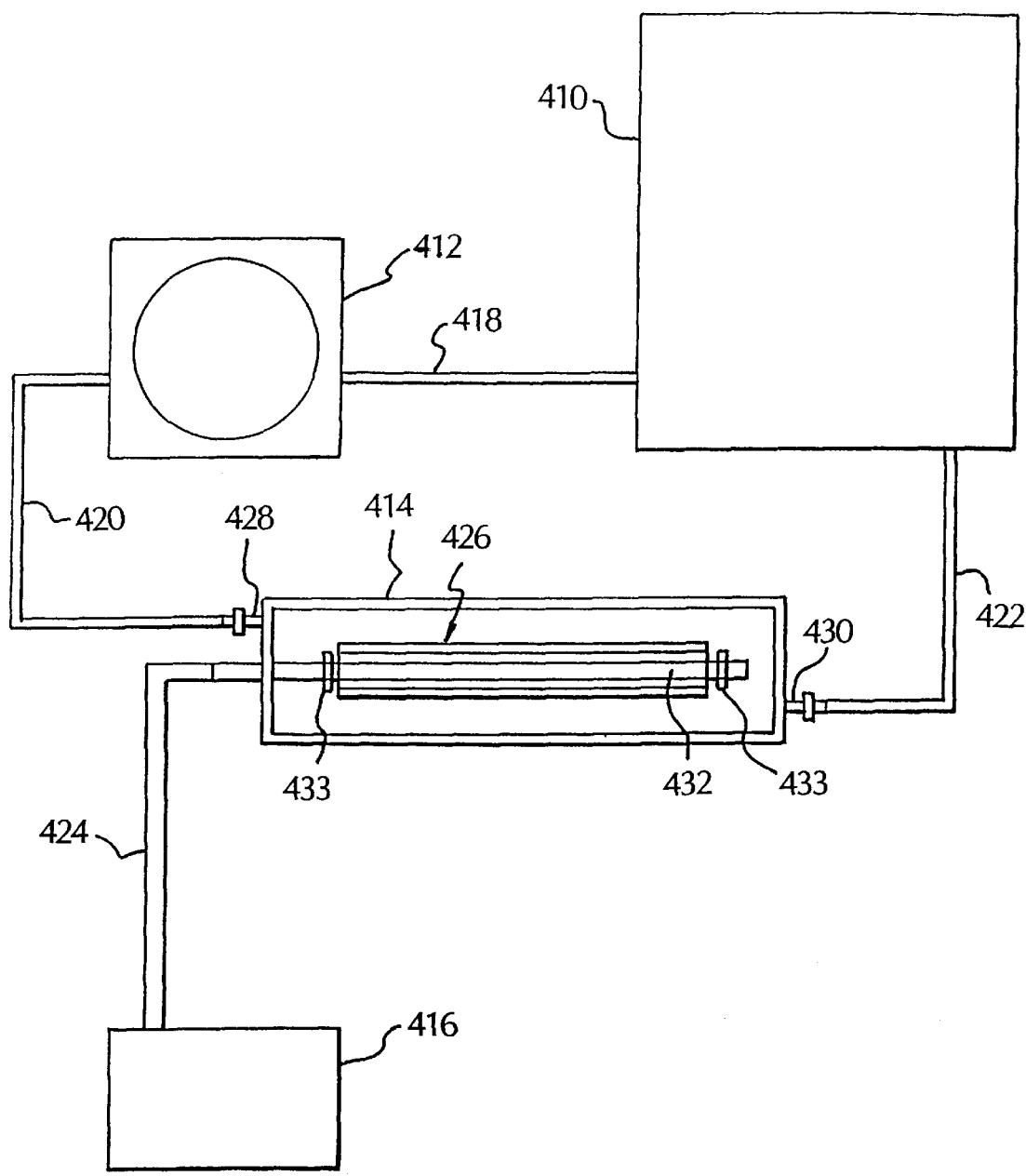
FIG. 12 is a schematic diagram illustrating an apparatus according to the present invention for sterilizing, seeding, culturing, storing, shipping, and testing a tubular prosthesis.

FIG. 12 discloses a system for sterilizing, seeding, culturing, storing, shipping, and testing vascular grafts. According to a preferred embodiment of the invention, this system primarily comprises a fluid reservoir 410, a pump 412, a treatment chamber 414, and an alternating pressure source 416.

Fluid reservoir 410 is used to store fluid for the system. Two illustrative suitable reservoirs are the Gibco-BRL 1L media bag and any rigid container capable of sterilization. Reservoir 410 may include a one way filter so as to provide a direct source of gas to the fluid within the system. Examples of fluid which may be used in the system include, but are not limited to, sterilizing fluid, tanning fluid, fluid containing cells, or fluid containing a culture medium. It is to be understood that during testing, seeding, and culturing in a preferred embodiment, the fluid may be advantageously kept at human body temperature, and may be composed of a fluid which approximates the viscosity of human blood. One illustrative example of a solution which approximates the viscosity of blood is saline with glycerol.

The fluid contained in reservoir 410 is retrieved through fluid line 418 by pump 412. Fluid line 418, as well as all other fluid lines in the system, may be made of any type of medical grade, durable tubing suitable for transporting the fluid in use. Pump 412 may be any fluid pump which can achieve variable flow rates. One such pump is the Masterflex L/S Digital Drive peristaltic pump manufactured by Cole-Palmer, although one skilled in the art could select from a variety of commercially available pumps. Pump 412 propels the fluid from reservoir 410 to treatment chamber 414 through fluid line 420.

Treatment chamber 414 preferably may be composed of any biocompatible, rigid material capable of being sterilized such as Teflon, polycarbonate, PVC, or stainless steel. However, it could also be made of a flexible material that could aid in the control of fluid volume surrounding the vascular grafts during culture or cryopreservation. Treatment chamber 414 may be comprised of two sections which are secured and made leak proof through any standard means such as inner and outer threads or the use of bonding agents. In order to view vascular grafts within treatment chamber 414, a viewing port may be placed at any point on the chamber, or alternatively, the chamber may be made of an optically clear material such as polycarbonate or PVC.

Inlet port 428 and outlet port 430 of treatment chamber 414 allow for the perfusion and/or circulation of fluid into and through the chamber. Inlet port 428 and outlet port 430 are also used to attach treatment chamber 414 to fluid lines 420 and 422 respectively. Fluid line 422 connects chamber 414 back to fluid reservoir 410 so as to create a closed system.

Treatment chamber 414 houses an expandable tube 432 upon which may be placed a vascular graft scaffolding 426.

As discussed in detail in both of the patents incorporated by reference below, scaffolding 426 may illustratively consist of any knitted, braided, woven, felted, or synthesized materials that are bioresorbable and/or biocompatible, as well as any native graft scaffolding material. Tube 432 may be comprised of any suitable elastomeric material, such as PET or silicone angioplasty balloons, which is capable of expanding and contracting. Treatment Chamber 414 and tube 432 may be made any length or diameter so as to hold a vascular graft scaffolding 426 of any length or diameter. This is advantageous, as the system may be used to sterilize, seed, culture, store, ship, and test vascular grafts of any size, such as coronary, carotid, iliac, and peripheral leg grafts. A porous clip or grommet 433 may be placed on tube 432 at both ends of scaffolding 426 to hold the scaffolding firmly in place on the tube during treatment. However, one skilled in the art will understand that any structure that allows for retention of the scaffolding 426 on tube 432 may be used. Grommets 433 are beneficial, as the tubing can be made smaller than the grafts so as to allow for the perfusion and/or circulation of fluids in between the graft and the tube, without the possibility of slippage of the graft on the tube.

Figure 13:
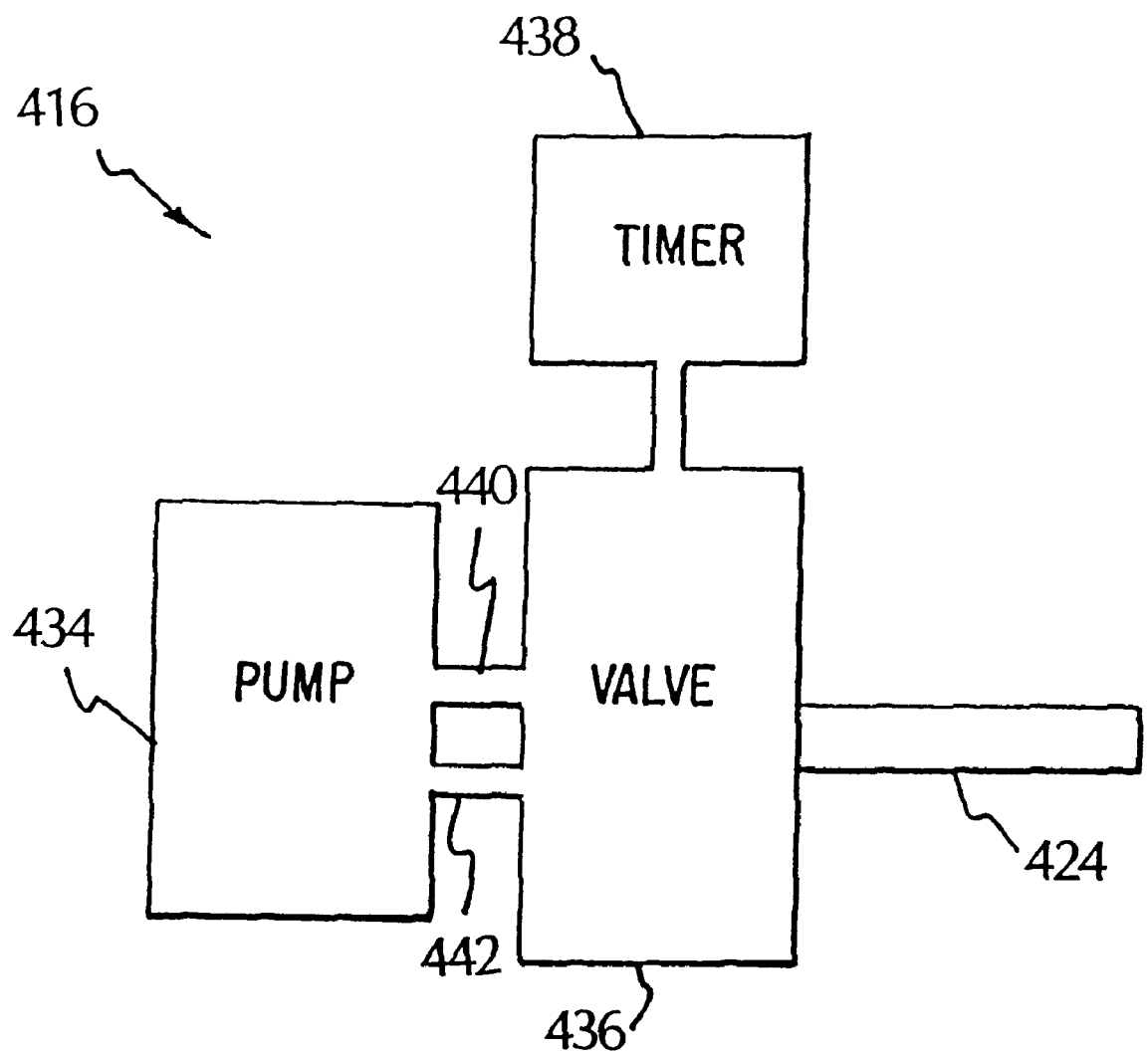
FIG. 13 is a block diagram illustrating a preferred embodiment of an alternating pressure source.

Tube 432 may be expanded and contracted by alternating pressure source 416, a preferred embodiment is shown in detail in FIG. 12. Specifically, FIG. 13 shows pump 434 which may be any standard pump capable of providing both positive pressure and negative (or vacuum) pressure, such as a piston or diaphragm pump. Valve 436 accepts the positive pressure and negative pressure from pump 434 through lines 440 and 442 respectively. Due to signals from timer 438, valve 436 causes alternating pressure to be applied to tube 432 from line 424. Valve 436 may be any type of in-line valve capable of directing and regulating multiple pressure lines. One such valve is the MAC 45S, model 45A-AA1-DAAA-1BA.

By expanding and contracting tube 432 with alternating pressure source 416, tube 432 places a varying radial stress on vascular graft scaffolding 426 simulating physiological conditions. This may produce a prosthesis that is more likely to tolerate physiological conditions found in the body.

Figure 14:
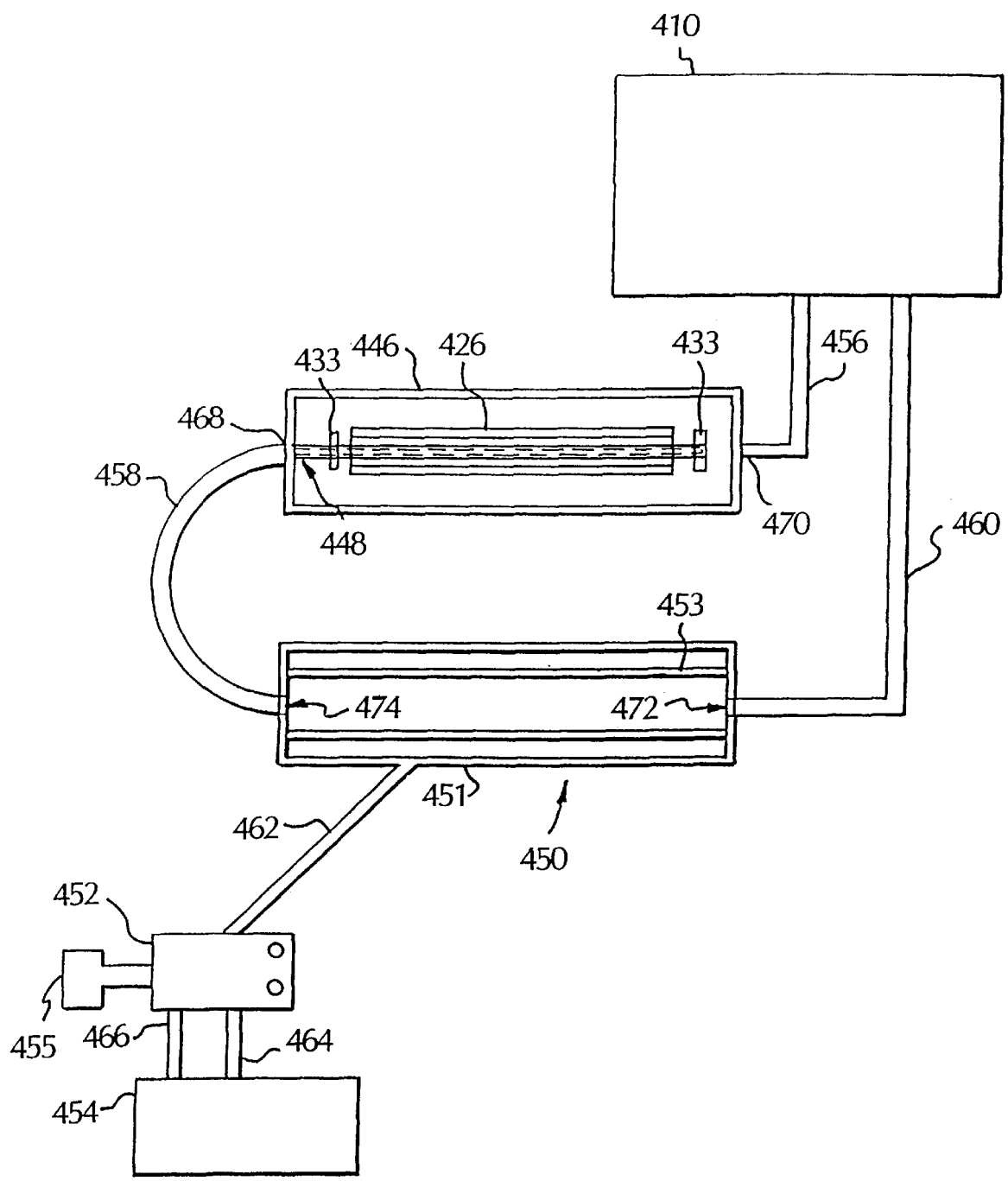
FIG. 14 is a schematic diagram illustrating another alternative exemplary embodiment of an apparatus according to the present invention for sterilizing, seeding, culturing, storing, shipping, and testing a tubular prosthesis.

FIG. 14 discloses an alternative embodiment of the invention for sterilizing, seeding, culturing, storing, shipping, and testing vascular grafts. According to this embodiment of the invention, the system primarily comprises a fluid reservoir 410, a bladder pump 450, a treatment chamber 446, and an alternating pressure source 454.

Fluid reservoir 410 and the fluids which it may contain are described in detail in conjunction with FIG. 12.

Treatment chamber 446 may be composed of any biocompatible, rigid material capable of being sterilized such as Teflon, polycarbonate, PVC, or stainless steel. Treatment chamber 446 may be comprised of two sections which are secured and made leak proof through any standard means such as inner and outer threads or the use of bonding agents. In order to view vascular grafts within treatment chamber 446, a viewing port may be placed at any point on the chamber, or alternatively, the chamber may be made of an optically clear material such as polycarbonate or PVC.

Treatment chamber 446 houses porous tube 448 upon which may be placed vascular graft scaffolding 426. Scaffolding 426 is discussed in detail in conjunction with FIG. 12. Porous tube 448 may be comprised of any suitable rigid material, such as Teflon, PVC, polycarbonate, or stainless steel, which may be made fluid permeable. One illustrative example of a suitable porous tubing is the porous plastic tubing manufactured by Porex Technologies. Alternatively, porous tube 448 may be comprised of any suitable elastomeric material, such as PET or angioplasty balloons, that is capable of expanding and contracting, and that may be made fluid permeable. Treatment Chamber 446 and tube 448 may both be made any length or diameter so as to hold vascular graft scaffolding 426 of any length or diameter. This is advantageous, as the system may be used to sterilize, seed, culture, store, ship, and test vascular grafts of any size. Porous clips or grommets 433 may be placed on tube 448 at both ends of scaffolding 426 to hold the scaffolding in place on the tube during treatment.

Inlet port 468 and outlet port 470 of treatment chamber 446 allow for the perfusion and/or circulation of fluid into and through the chamber. Inlet port and outlet port 470 are also used to attach treatment chamber 446 to fluid lines 458 and 456 respectively. Fluid line 56 connects chamber 46 back to fluid reservoir 410 so as to create a closed system. It is to be understood that although only one treatment chamber 446 is shown in FIG. 14, fluid lines 456, 458, and 460 may be branched so as to connect more than one treatment chamber in parallel to the system.

The fluid contained in reservoir 410 is retrieved through fluid line 460 by bladder pump 450. Fluid line 460, as well as all other fluid lines in the system, may be made of any type of medical grade, durable tubing suitable for transporting the fluid in use. Bladder pump 450 is comprised of a pneumatic pressure chamber 451 and a bladder 453, which may be comprised of a suitable elastomeric material. An illustrative suitable bladder is the Cutter/Miles double valved hand activated blood pump. Bladder pump 450 forces fluid from reservoir 410 to treatment chamber 446 through fluid line 458 by being alternately compressed and expanded by alternating pressure source 454 in conjunction with valve 452 and timer 455. Alternating pressure source 454 preferably may be any standard pump capable of providing positive and negative (or vacuum) pressure, such as a piston or diaphragm pump. Valve 452 accepts the positive pressure and negative pressure from pump 454 through lines 464 and 466, respectively. Due to signals from timer 455, valve 452 causes alternating positive and negative pressure to be applied to bladder 453 from line 462. Valve 452 may be any type of in-line valve capable of directing and regulating multiple lines. One such valve is the MAC 45S, model 45A-AA1-DAAA-1BA.

When negative pressure is applied to bladder 453, fluid will be drawn from fluid reservoir 410 through fluid line 460 until bladder 453 is filled with fluid and is in an expanded state. During expansion of bladder 453, check valve 474 will ensure that no fluid is drawn from fluid line 458. Once the signal from timer 455 causes a positive pressure to be applied to bladder 453, the fluid contained in the bladder is forced out of the bladder and through fluid line 458 to treatment chamber 446. When fluid is forced out of bladder 453, check valve 472 will ensure that no fluid is forced back into fluid line 460. This causes, a pulsitile, cyclic fluid flow to treatment chamber 446 through tube 448 and out of port 470.

If tube 448 is comprised of a rigid porous material, then the varying fluid pressure caused by the action of bladder pump 50 will force fluid to flow through the porous material. The fluid flow through the porous material will place a varying radial stress on vascular graft scaffolding 426. Alternatively, if tube 448 is comprised of a porous elastomeric material, tube 448 may be expanded and contracted by the varying fluid pressure provided by bladder pump 450. By expanding and contracting porous tube 448 with bladder pump 450, tube 448 places a varying radial stress on vascular graft scaffolding 426. Moreover, as is the case with a rigid tube 448, the fluid flow through the elastomeric porous material will also place a varying radial stress on scaffolding 426. This places a cyclical radial stress on the scaffolding and cells supported thereon. This produces vascular grafts that are more likely to tolerate the physiological conditions found in the human body.

Seeding and culturing of the vascular graft in treatment chambers 414 and 446 is generally accomplished by known techniques, with the added benefits and advantages gained from the radial and/or shear stresses placed upon the vascular graft during growth. Examples of suitable seeding and culturing methods for the growth of three-dimensional cell cultures are disclosed in U.S. Pat. No. 5,266,480, which is incorporated herein by reference. The techniques described in U.S. Pat. No. 5,266,480 for establishing a three-dimensional matrix, inoculating the matrix with the desired cells, and maintaining the culture may also be readily adapted by a person of ordinary skill in the art for use with the present invention.

Once the vascular graft has reached the desired level of cell density, a preservative may then be pumped into treatment chamber 414 or 446. Once the treatment chambers are filled with the preservative, the inlet ports and outlet ports of the chambers may be closed, again creating a sealed chamber which may then be used to store and/or ship the cultured and preserved vascular graft. Preferably, the preservative is a cryo-preservative so that the graft may be frozen in chamber 414 or 446. In this manner, sealed treatment chamber 414 or 446 may be used to sterilize, culture, store, and ship vascular grafts or other prostheses. store, and ship heart valves or other prostheses.

Further details of the apparatus according to the present invention for sterilizing, seeding, culturing, storing, shipping, and testing tubular prostheses are found in U.S. Pat. No. 5,792,603, which is incorporated herein by reference.

We claim:

1. An apparatus for growth of tissue for implantation in a human or animal body, comprising:
    a substrate designed to facilitate three-dimensional tissue growth on said substrate, said substrate comprising a biocompatible, non-living three-dimensional framework having interstitial spaces bridgeable by cells;
    a housing defining a tissue growth chamber;
    a support structure located within said chamber configured and dimensioned to support said substrate; and
    means for simulating the physiological conditions to be encountered by the tissue once implanted, said simulating means comprising means for controlling media flow characteristics around said substrate mounted on said support structure within said housing.

2. The apparatus of claim 1, wherein said housing includes a first port and a second port for flow of media therethrough.

3. The apparatus of claim 2, wherein said controlling means controls media flow characteristics around said substrate as said media flows from the first port through said chamber to the second port to impart at least one of radial, shear or axial stresses to said substrate.

4. The apparatus of claim 3, wherein said controlling means includes a pump in fluid communication with said first and second ports.

5. The apparatus of claim 1, wherein said substrate is configured and dimensioned as a heart valve.

6. The apparatus of claim 1, wherein said substrate is configured and dimensioned as a vascular graft.

7. The apparatus of claim 1, wherein said substrate is configured and dimensioned as a cartilage graft, a ligament construct or a tendon construct.

8. The apparatus of claim 1. wherein said simulating means further comprises
    means for moving said support structure between a first position and a second position, such that movement of said support structure between said positions creates varying stresses in the substrate supported thereby, said varying stresses simulating the physiological conditions to be encountered by tissue grown on said substrate once implanted.

9. The apparatus of claim 8, wherein said housing includes a first port and a second port for flow of media therethrough.

10. The apparatus of claim 9, wherein said simulating means further comprises a pump in fluid communication with said first and second ports.

11. The apparatus of claim 8, wherein said support structure comprises a piston secured to an end of the substrate.

12. The apparatus of claim 8, wherein the support structure comprises an expandable member that is adapted to receive the substrate thereover.

13. The apparatus of claim 8, wherein the support structure comprises a bellows secured to an end of the substrate.

14. The apparatus of claim 8, wherein said substrate is configured and dimensioned as any of a vascular graft, a cartilage construct, a ligament construct or a tendon construct.

15. The apparatus of claim 8, wherein said substrate is a ligament substrate or a tendon substrate.

16. An apparatus for tissue growth, comprising:
    a housing defining a seeding and culturing chamber;
    a substrate disposed within said chamber designed to facilitate three-dimensional tissue growth on said substrate, said substrate comprising a three-dimensional framework having interstitial spaces bridgeable by cells;
    a support structure located within said chamber configured and dimensioned to support the substrate;
    means for controlling media flow characteristics around said substrate within said chamber; and
    means for imparting an axial stress to the substrate mounted on said support structure within said chamber.

17. The apparatus of claim 16, wherein said housing includes a first port and a second port for flow of fluid media therethrough.

18. The apparatus of claim 17, wherein said controlling means comprises a pump fluidly connected to said first and second ports for providing varying fluid flow and pressure within said chamber.

19. The apparatus of claim 17, wherein the first and second ports of said housing may be sealed for enclosing, sterilizing, storing, and shipping the substrate.

20. The apparatus of claim 16, wherein said imparting means comprises a means for applying an axial magnetic load to the substrate.

21. The apparatus of claim 16, wherein said imparting means comprises a means for applying an axial mechanical load to the substrate.

22. The apparatus of claim 21, wherein said applying means comprises a piston.

23. The apparatus of claim 21, wherein said applying means comprises a bellows.

24. The apparatus of claim 21, wherein said imparting means comprises a flexible diaphragm.

25. The apparatus of claim 16, wherein said support structure comprises a plurality of sutures.

26. The apparatus of claim 16, further comprising a three-dimensional tissue, said tissue comprising a plurality of cells attached to and substantially enveloping said framework.

27. The apparatus of claim 26, wherein said substrate is a tendon substrate or a ligament substrate.

28. The apparatus of claim 16, wherein said imparting means comprises said means for controlling media flow characteristics.

29. A method for seeding and culturing a substrate, comprising:

exposing plural sides of a substrate to a flowing fluid media for seeding and culturing, said substrate designed to facilitate three-dimensional tissue growth on said substrate, said substrate comprising a three-dimensional framework having interstitial spaces bridgeable by cells; and imparting an axial stress to the substrate during said seeding and culturing to encourage a desired alignment of cells on the substrate.

30. The method of claim 29, wherein said step of imparting axial stress comprises:

attaching said substrate to a support structure; and moving said support structure between a first position and a second position so that axial stress is imparted to the substrate.

31. The method of claim 30, wherein the length of said substrate is varied by said step of moving said support structure.

32. The apparatus of claim 29, wherein said substrate is a tendon substrate or a ligament substrate.

33. A method for seeding and culturing a substrate, comprising:

exposing plural sides of a substrate to flowing fluid media for seeding and culturing, said substrate designed to facilitate three-dimensional tissue growth on said substrate, said substrate comprising a three-dimensional framework having interstitial spaces bridgeable by cells; and imparting stresses to the substrate during said seeding and culturing to simulate the physiological conditions to be encountered by the tissue grown on said substrate once implanted, thereby encouraging a desired alignment of cells on the substrate.

34. The method of claim 33, wherein said step of imparting stresses comprises:

placing said substrate on a support structure; and moving said substrate between a first position and a second position so that stress is imparted to the substrate.

35. The method of claim 33, wherein said step of imparting stresses comprises:

placing said substrate on a support structure; and controlling media flow characteristics around said substrate mounted on said support structure.

36. The method of claim 35, wherein said step of imparting stresses further comprises changing fluid pressure around said substrate.

37. The method of claim 36, wherein altering said pressure change moves said substrate between a first position and a second position.

38. The apparatus of claim 33, wherein said substrate is a tendon substrate or a ligament substrate.

\* \* \* \* \*